(12) United States Patent
Weber et al.

(10) Patent No.: US 7,479,157 B2
(45) Date of Patent: Jan. 20, 2009

(54) STENT DESIGNS WHICH ENABLE THE VISIBILITY OF THE INSIDE OF THE STENT DURING MRI

(75) Inventors: Jan Weber, Maple Grove, MN (US); Thomas J. Holman, Princeton, MN (US); James Heggestuen, Stillwater, MN (US); Barry J. O'Brien, Barna Galway (IR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 727 days.

(21) Appl. No.: 10/636,063

(22) Filed: Aug. 7, 2003

(65) Prior Publication Data

US 2005/0033407 A1    Feb. 10, 2005

(51) Int. Cl.
  *A61M 29/00* (2006.01)
(52) U.S. Cl. .................................... 623/1.15
(58) Field of Classification Search ........... 623/1.15, 623/1.16–1.22, 1.11; 606/192, 194, 195, 606/198
See application file for complete search history.

(56) References Cited

U.S. PATENT DOCUMENTS

| | | | | |
|---|---|---|---|---|
| 5,035,706 | A | 7/1991 | Giantureo et al. | 606/198 |
| 5,135,536 | A | 8/1992 | Hillstead | 606/195 |
| 5,170,789 | A | 12/1992 | Narayan et al. | 128/653.5 |
| 5,405,377 | A | 4/1995 | Cragg | 623/1 |
| 5,445,151 | A | 8/1995 | Darrow et al. | 128/653.3 |
| 5,655,155 | A | 8/1997 | Bergstresser et al. | 396/6 |
| 5,755,781 | A | 5/1998 | Jayaraman | 623/1 |
| 5,843,120 | A | 12/1998 | Israel et al. | 606/198 |
| 5,916,264 | A | 6/1999 | Von Oepen et al. | 623/1 |
| 6,168,621 | B1 | 1/2001 | Vrba | 623/1.2 |
| 6,231,516 | B1 | 5/2001 | Keilman et al. | 600/485 |
| 6,280,385 | B1 | 8/2001 | Melzer et al. | 600/423 |
| 6,340,367 | B1 | 1/2002 | Stinson et al. | 623/1.34 |
| 6,463,317 | B1 | 10/2002 | Kucharczyk et al. | 600/411 |
| 6,537,310 | B1 | 3/2003 | Palmaz et al. | 623/1.13 |
| 6,585,755 | B2 | 7/2003 | Jackson et al. | 623/1.15 |
| 6,585,763 | B1 | 7/2003 | Keilman et al. | 623/1.42 |
| 6,712,844 | B2 * | 3/2004 | Pacetti | 623/1.15 |
| 6,866,805 | B2 * | 3/2005 | Hong et al. | 264/161 |
| 2002/0138133 | A1 | 9/2002 | Lenz et al. | |
| 2002/0188345 | A1 | 12/2002 | Pacetti | |

FOREIGN PATENT DOCUMENTS

| | | |
|---|---|---|
| WO | WO 93/13825 | 7/1993 |
| WO | WO 96/26689 | 9/1996 |
| WO | WO 00/12147 | 3/2000 |
| WO | WO 01/08600 | 2/2001 |

OTHER PUBLICATIONS

International Search Report received in PCT/US2004/025492, mailed Sep. 14, 2005.

* cited by examiner

*Primary Examiner*—Kevin T Truong
(74) *Attorney, Agent, or Firm*—Fish & Richardson P.C.

(57) ABSTRACT

A medical device that inhibits distortion of medical resonance images taken of the device. In particular, various structures are utilized to allow visibility proximate, and inside of, a tubular member, such as a stent. In one embodiment, the stent is constructed such that any closed path encircling at least a circumference of the stent will pass through at least two materials to reduce or eliminate electrical loops formed in the stent.

21 Claims, 15 Drawing Sheets

STENT DESIGNS WHICH ENABLE THE VISIBILITY OF THE INSIDE OF THE STENT DURING MRI

BACKGROUND OF THE INVENTION

The present invention relates generally to devices for use in vascular treatments. More particularly, the present invention relates to devices used in vascular treatments that incorporate a magnetic resonance visibility enhancing structure, the devices being adapted for use in magnetic resonance imaging.

Vascular stents are known medical devices used in various vascular treatments of patients. Stents commonly include a tubular member that is moveable from a collapsed, low profile, delivery configuration to an expanded, deployed configuration. In the expanded configuration, an outer periphery of the stent frictionally engages an inner periphery of a lumen. The deployed stent then maintains the lumen such that it is substantially unoccluded and flow therethrough is substantially unrestricted. However, various stent designs substantially distort the surrounding of the stent during a Magnetic Resonance Imaging procedure.

Magnetic Resonance Imaging (MRI) is a non-invasive medical procedure that utilizes magnets and radio waves to produce a picture of the inside of a body. An MRI scanner is capable of producing pictures of the inside of a body without exposing the body to ionizing radiation (X-rays). In addition, MRI scans can see through bone and provide detailed pictures of soft body tissues.

A typical MRI scanner includes a magnet that is utilized to create a strong homogeneous magnetic field. A patient is placed into or proximate the magnet. The magnetic field causes a small majority of the atoms with a net magnetic moment, also referred to as spin, to align in the same direction as the magnetic field. When a radio wave is directed at the patient's body, atoms precessing in the magnetic field with a frequency equal to the radiowave are able to adapt the radiowave energy, which causes them to "tumble over" and align in the opposite direction of the magnetic field. The frequency at which atoms with a net spin precess in a magnetic field is also referred to as the Larmor frequency. The opposing alignment is at a higher energy level compared to the original orientation. Therefore, after removing the radiowave, atoms will return to the lower energetic state. As the atoms return to the lower energetic state, a radio signal is sent at the Lamor frequency. These return radio waves create signals (resonance signals) that are detected by the scanner at numerous angles around the patient's body. The signals are sent to a computer that processes the information and compiles an image or images. Typically, although not necessarily, the images are in the form of 2-dimensional "slice" images.

An ability to effectively view areas proximate a stent during an MRI procedure is desirable. In particular, viewing areas inside and proximate a tubular member of a stent may be desirable both during deployment and after deployment of the stent in a patient. However, various current stent designs prevent adequate imaging of the area surrounding the stent. Instead, the images are distorted and thus cannot be used.

The visibility of the inside of current stent designs during MRI procedures is blocked for two reasons. First of all, the permanent influence of the surrounding magnetic field by stents containing ferromagnetic materials prevents adequate imaging. A second reason that adequate imaging of the area inside the stent is blocked relates to induction currents (Eddy currents), induced in the closed cell metal stent structure due to the changes in the magnetic field generated by the MRI system during image sequencing. The result is that the MR visibility of the inside of the stent is shielded.

It is possible to build a stent out of polymer or other non-conducting materials such as ceramics. Building stents out of such non-conducting materials would avoid either of these MR artifacts. However, stents made from materials such as these would require larger strut dimensions to maintain adequate stent mechanical performance as compared to stents made of metals.

The present invention addresses at least one of these or other problems, and/or offers other advantages over the prior art.

SUMMARY OF THE INVENTION

Embodiments of the present invention relate to medical devices that reduce the distortion of medical resonance images taken of the devices. In particular, various structures are utilized to enhance visibility proximate and inside of a tubular member of a stent. In one particular embodiment, the stent is constructed such that any closed path encircling at least a circumference of the stent will pass through at least two materials to reduce or eliminate electrical currents formed in the stent as a result of changing electromagnetic fields passing through the stent.

DETAILED DESCRIPTION OF ILLUSTRATIVE EMBODIMENTS

Figure 1:
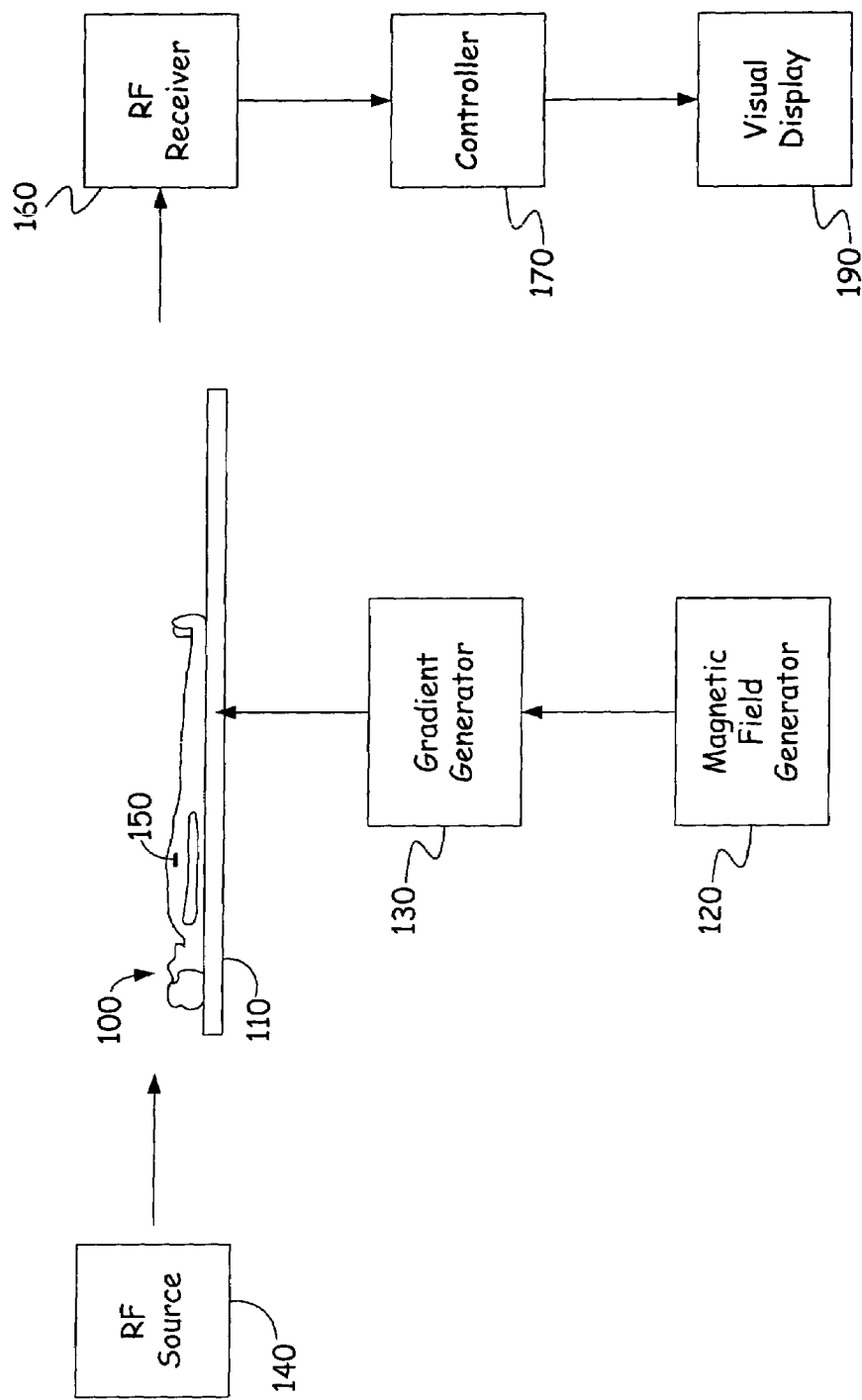
FIG. 1 is a partial block diagram of an illustrative magnetic resonance imaging system.

FIG. 1 is a partial block diagram of an illustrative magnetic resonance imaging system. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a stent, has been inserted, is located in the body of subject 100.

RF source 140 radiates pulsed radio frequency energy into subject 100 and stent 150 at predetermined times and with sufficient power at a predetermined frequency to influence nuclear magnetic spins in a fashion known to those skilled in the art. The influence on the spins causes them to position anti-parallel to the main magnetic field when the radio frequency equals the Larmor frequency of the atoms, allowing them to accept the radio energy. As atoms can only accept radio energy when the radio frequency equals their Larmor frequency, which is directly related to absolute magnetic field strengths, one is able to selectively change the net-spin of only certain regions by using additional gradient magnetic fields. The Larmor frequency for each spin is directly proportional to the absolute value of the magnetic field experienced by the atom. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils such as surface coils may alternatively be used.

External RF receiver 160 illustratively detects RF signals emitted by the subject in response to the radio frequency field created by RF source 140. In an illustrative embodiment, external RF receiver 160 is a cylindrical external coil that surrounds the region of interest of subject 100. Such an external coil can have a diameter sufficient to encompass the entire subject 100. External RF receiver 160 can share some or all of its structure with RF source 140 or can have a structure entirely independent of RF source 140. The region of sensitivity of RF receiver 160 is larger than that of the stent 150 and can encompass the entire subject 100 or a specific region of subject 100. The RF signals detected by external RF receiver 160 are sent to imaging and tracking controller unit 170 where they are analyzed. Controller 170 displays signals received by RF receiver 160 on visual display 190.

Establishing a homogenous, or uniform, magnetic field with magnetic field generator 120 in addition to switched linear gradient magnetic fields activated in various sequences as well as timely switching the RF radiowave in various sequences, as known in the art, enables the production of internal images of subject 100. It is common that the magnetic field surrounding stent 150 is distorted, which causes distortion of images obtained proximate stent 150. This is because the magnetic field distortion due to the ferromagnetic components will change the absolute magnetic field proximate to the stent causing in effect shifts in the Larmor frequencies which changes the interaction with the RF-field (amplifies, reduces or even eliminates the interaction). For example, it is common for the material and structure of stent 150 to affect the magnetic field around stent 150. Such effects reduce the influence that magnetic field generator 120, gradient generator 130 and RF source 140 have on the nuclear magnetic spins in subject 100. In particular, the spins inside a tubular member of a stent are commonly not excited during an MRI and thus no image is detected.

One embodiment of the present invention includes using non-ferromagnetic materials in stent 150 to reduce this distortion. Such materials include, by way of example, platinum, iridium, tantalum, titanium, gold, niobium, hafnium alloys exhibiting non-ferromagnetic properties, and other non-ferromagnetic materials. Combinations of ferromagnetic and non-ferromagnetic materials and/or non-metal material can also be utilized without departing from the scope of the present invention.

Another effect that commonly distorts the magnetic field around an intravascular device is associated with Faraday's Law. Faraday's Law simply states that any change in a magnetic environment of a coil will cause a voltage (emf) to be "induced" in the coil. Stent 150 can act as a coil when implanted in a subject during an MRI process. The change in magnetic environment is caused either by stent 150 moving or rotating within a nonuniform magnetic field, or by changes in the magnetic field proximate stent 150. For example, stent 150 may move due to the heart beating or magnetic field changes may be induced by gradient generator 130 or RF Source 140.

According to Faraday's Law, the induced emf in a coil is equal to the negative of the rate of change of magnetic flux through the coil times the number of turns in the coil. When an emf is generated by a change in magnetic flux, the polarity of the induced emf produces a current creating a magnetic field that opposes the change which produces it. Accordingly, the induced magnetic field inside any loop of wire acts to keep the magnetic flux inside the loop constant. In the case of a metallic stent, where each individual ring or cell, or combinations of cells, can act as a coil, the visibility within and around or adjacent the stent using an MRI can be blocked.

Figure 2:
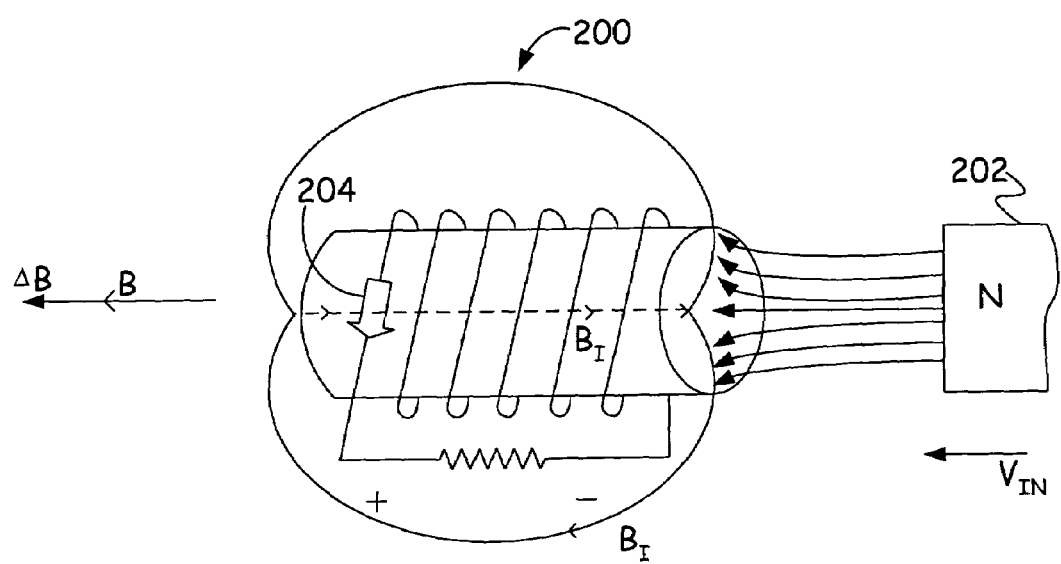
FIG. 2 is an illustration of a coil in a changing magnetic field.

FIG. 2 further illustrates this effect. Coil 200 has been placed in a magnetic field produced by magnet 202. The magnetic field is represented by a vector B. Any change in magnetic field B, herein represented as ΔB, causes a current, represented as arrow 204, to be produced in coil 200. Current 204 causes a magnetic field $B_I$ to be induced, which opposes the change ΔB.

When attempting to produce an image of stent 150 inside subject 100, some stents act as a coil or, depending on the structure of the stent, as multiple coils. During various phases of an MRI process to influence the nuclear spins, a change in the magnetic field inside the stent is generated. For example, gradient generator 130 may generate a pulse in order to influence spins to be analyzed by controller 170. The gradient generator 130 thus changes the magnetic field and accordingly a change in magnetic field proximate the stent is opposed by Faraday's Law. As a result, spins proximate the stent are not excited and images of the stent show a lack of signal.

In order to reduce the effect of Faraday's Law on spins inside the stent loops or the main stent tube, various stent designs have been made in accordance with embodiments of the present invention. In some embodiments, the creation of electrical loops within a stent structure is avoided by eliminating electrical loops within the cells or rings of the stents. These embodiments are described below with reference to various examples. However, the invention is not limited to these examples. Using these designs, the visibility of a stent during an MRI process is enhanced by removal of the desired artifacts.

Figure 3:
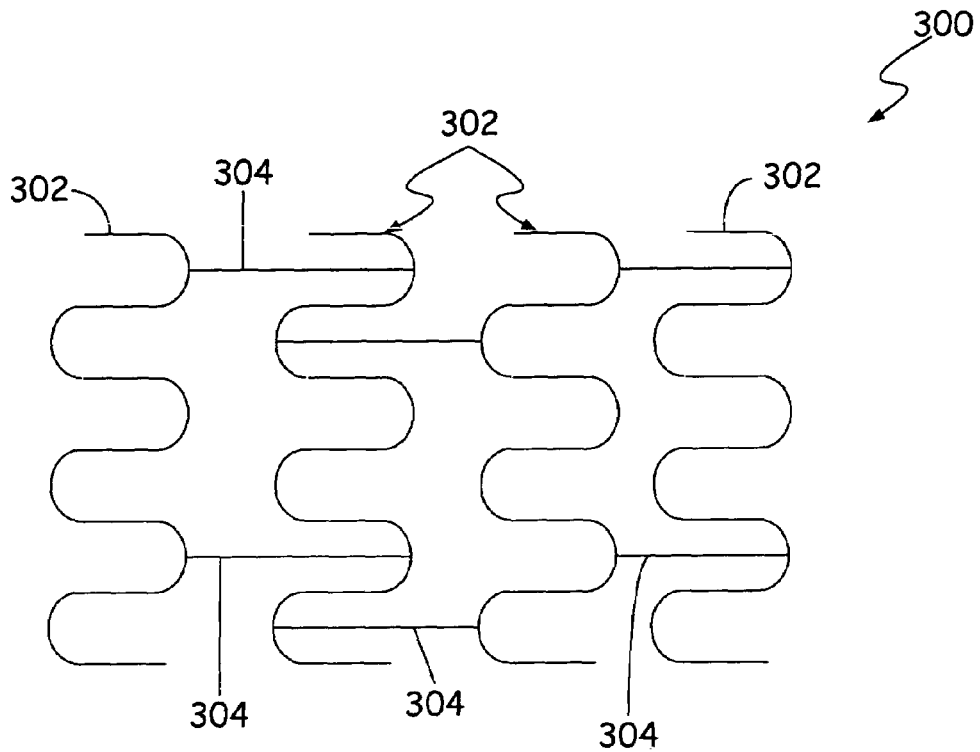
FIG. 3 is a diagrammatic side view of a portion of a stent showing a cell and connector structure.

Referring now to FIG. 3, illustrated is a portion of a stent 300 which can be one embodiment of stent 150 shown in FIG. 1. As shown diagrammatically in FIG. 3, stent 300 includes a plurality of cells (sometimes referred to as struts, bands or rings) 302 which are connected together using a plurality of connectors (sometimes referred to as bridges or links) 304. The cells 302 are wrapped around a central axis (not shown) to form a generally tubular structure. Cells 302 and/or connectors 304 can be made of a material that is substantially non-ferromagnetic. When expanded, cells 302 and connectors 304 frictionally engage an inner periphery of a lumen when a tubular structure of stent 300 is opened to support the anatomy. Although cells 302 and connectors 304 can be made of a non-ferromagnetic material to reduce the permanent influence on the surrounding magnetic fields, if cells 302 are made from electrically conductive material, each cell 302 can circumferentially form a closed electrical loop. Closed electrical loops act as coils and negatively impact the visibility of a region proximate the inside of the stent during an MRI. Multiple loops can be laterally or longitudinally formed, with a single electrical loop sometimes traversing multiple cells 302 via connectors 304.

This problem can be overcome by constructing the stent using non-ferromagnetic metals (i.e., having low magnetic susceptibility) to overcome the first mentioned hurdle, and to include electrically non-conducting portions within each cell 302 to overcome the issue of induction currents by eliminating electrical loops formed circumferentially within the cells. The electrically non-conducting portions can also be included within specific connectors 304 to eliminate closed electrical loops longitudinally traversing multiple cells 302. In some embodiments, further operational enhancement is achieved by including an isolating coating around at least some necessary metal parts of the stent to eliminate any problematic electrical bridge through the surrounding media (e.g., blood).

Figure 4:
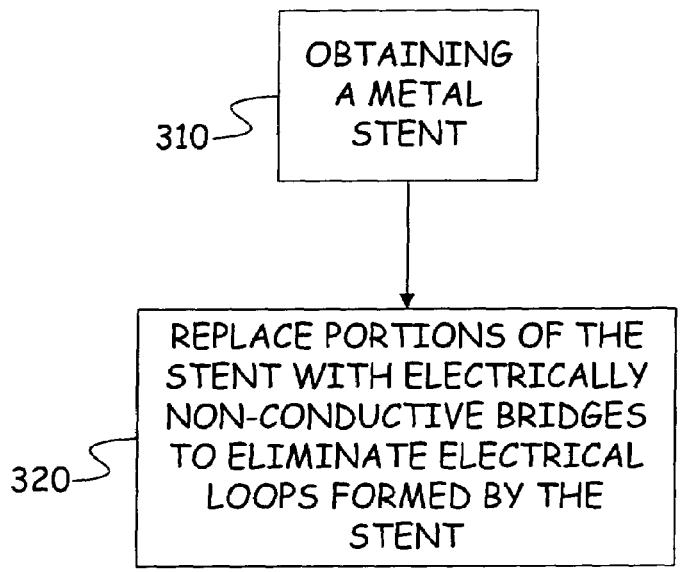
FIG. 4 is a block diagram illustrating a method of the present invention.

FIG. 4 is a block diagram illustrating a general method of producing stents which enable the visibility of the inside of the stent during MRI. Using this method, a metal stent is obtained as is shown in step 310. Then, portions of the stent are replaced with electrically non-conductive bridges to reduce or minimize the electrical loops formed in the stent. This is illustrated at step 320 in FIG. 4. In some embodiments, these steps are used to create stents in which any closed path encircling at least the circumference of the stent will pass through at least two materials. If at least one of the materials is electrically non-conductive, electrical currents will be reduced or eliminated. The present invention is not limited to this particular method, and includes, for example, methods of forming stents which do not alter an existing metallic stent.

In various embodiments of the invention, step 320 of replacing portions of the stent with electrically non-conductive bridges includes replacing at least a portion of each cell 302 with the electrically non-conductive struts to eliminate closed electrical loops formed by each individual cell. In some embodiments, step 320 further includes replacing portions of each connector 304 with electrically non-conductive bridges to eliminate closed electrical loops formed between cells 302 in the stent. Various more specific methods of fabricating stents in accordance with the method shown in FIG. 4 are described below. Further, other methods can be used to produce stents in accordance with the invention in which any closed path encircling at least the circumference of one cell will pass at least through two materials.

In some embodiments of the invention, the electrically non-conductive struts placed or formed in the cells 302 and connectors 304 are ceramic struts or bridges, respectively. A typical example of the use of a strong ceramic material in the human body in combination with a metal structure is the case of dental crowns. In that example, the connection between the metal and the porcelain is made by applying ceramic powder (Frit), with water or other liquid in slurry form. The liquid is evaporated and the assembly is fired at high temperature where frit is scintered into a solid ceramic with a strong bond to the metal base. Another technique for example is referred to as "press to metal". In that example the connection between the metal base structure with wax in the shape of a tooth and channels to direct the flow of molten ceramic in a mold (for example, phosphate bonded silica). Wax is eliminated to form a negative mold and ceramic ingots are molted and pressed into the mold. When cooled the solid ceramic with strong bond to metal base structure is divested with media blasting.

Figure 5A:
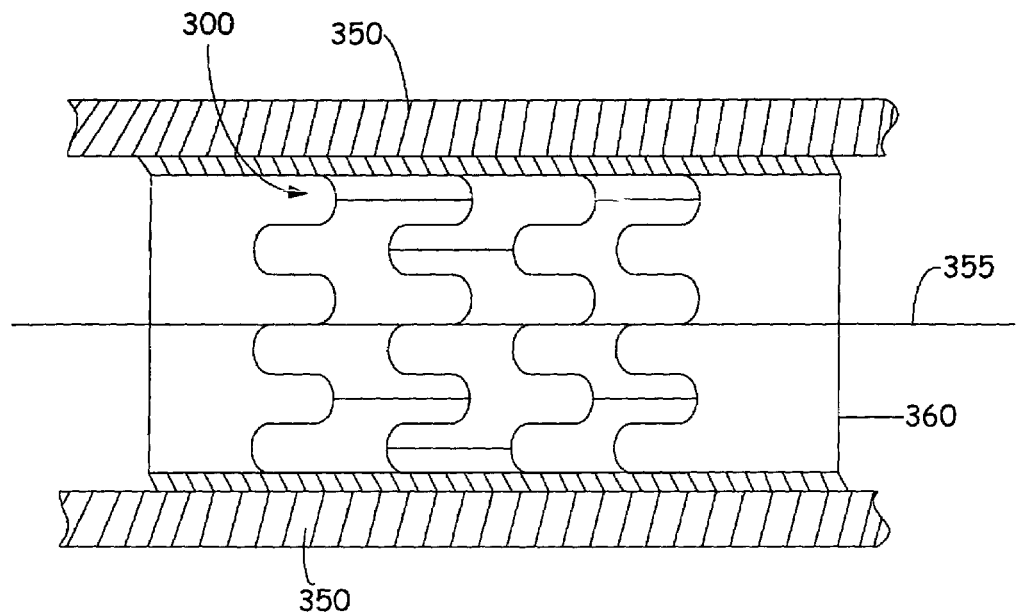
FIGS. 5A-5G are diagrammatic side view illustrations demonstrating implementation of the method shown in FIG. 4 in one particular embodiment.
Figure 5B:
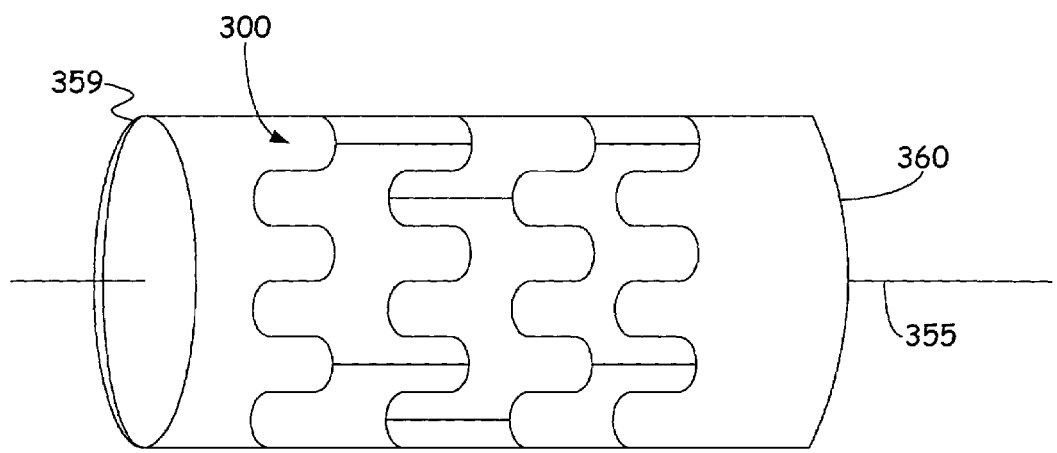

This type of process can be adapted to produce stents having ceramic bridges, for example as follows. In one embodiment, this type of process begins with obtaining a metal stent as was illustrated at step 310 in FIG. 4. In other words, a metal stent could be produced in a conventional fashion, including the lasercutting and electropolishing steps. Then, as illustrated in FIG. 5A, the stent 300 (only a portion of which is shown for sake of clarity) is positioned in a polymer or Teflon tube 350 (shown diagrammatically in cross-section in FIG. 5A) having an inner diameter which is only slightly larger than the outer diameter of the stent 300. The tube 350 is then filled with a material which hardens around stent 300. For example, the tube can be filled with an investment casting material (such as phosphate-bonded silica or gypsum solution), and subsequently dried or baked to solidify the gypsum around stent 300. Prior to hardening the gypsum or other tube filling material, a central corewire 355 can be placed on the central longitudinal axis of stent 300 to reinforce the gypsum structure and to provide a positioning device for subsequent laser cutting steps. Removal of the tube 350 leaves a solid gypsum rod 360 with the outer surface of the stent covered with a thin layer 359 of gypsum as is shown in FIG. 5B.

Figure 5C:
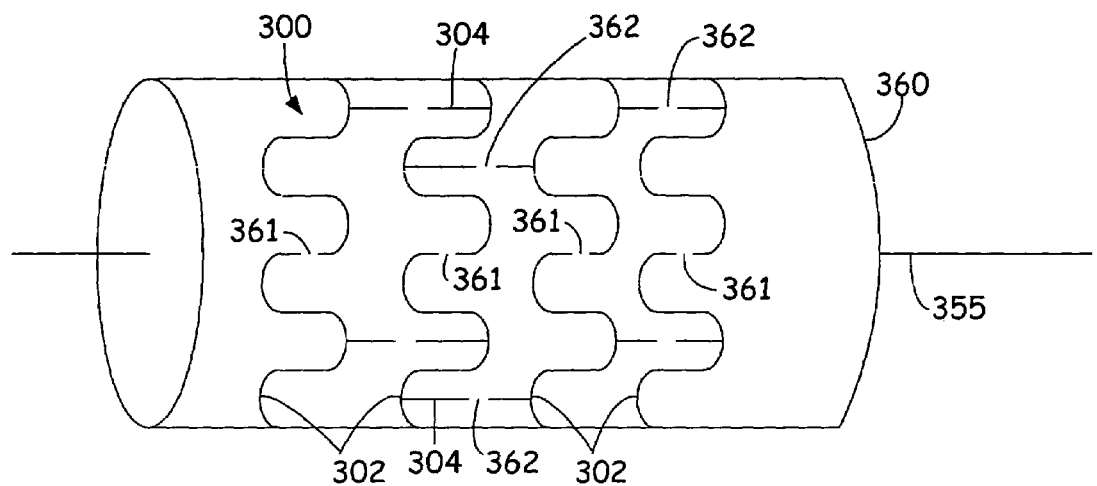
Figure 5D:
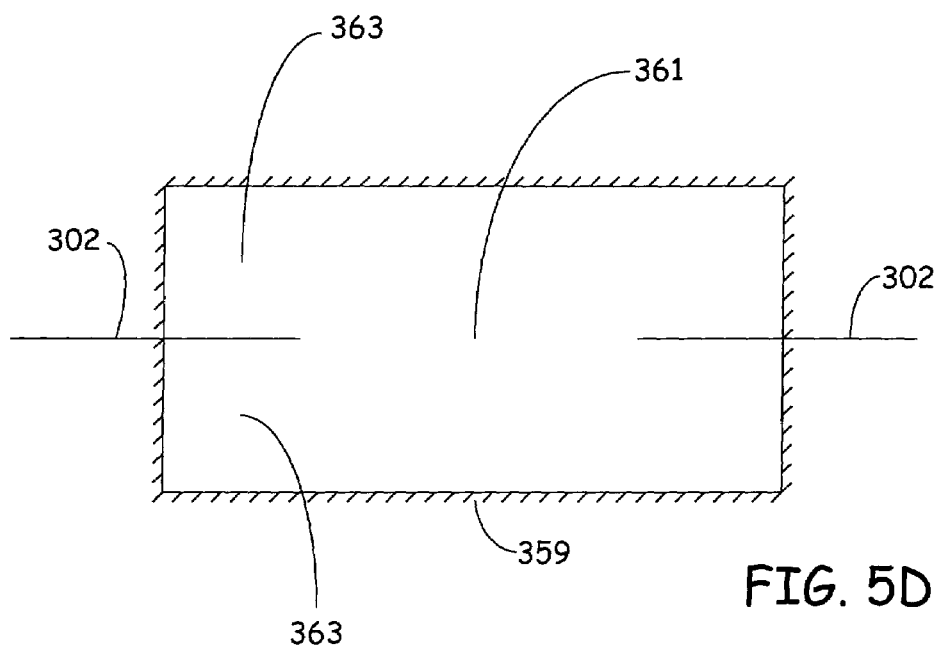

Next, a laser cutting process is used to cut through specific portions of cells 302 and connectors 304. The cuts or slits in the cells 300 are shown in FIG. 5C and are designated with reference number 361. The cuts or slits in the connectors 304 are also shown in FIG. 5C and are cells 302, and the cuts 362 in connectors 304, are made in places where ceramic connectors or bridges are to be formed. The laser cutting process is also used to produce openings where mechanical connections are to be formed for the ceramic in both sides of the slits 361, 362. FIG. 5D diagrammatically illustrates that the laser cutting process not only cuts away the gypsum in the area that defines the slit 361, but it also cuts away an area around slit 361. These exposed areas or openings on either side of slit 361 are referred to as openings 363 and they expose an area where mechanical connections are to be formed. These openings 363 are formed around each of slits 361, 362 in the cells and connectors.

Since the stent is embedded in the gypsum rod, the remaining structure is supported and kept in place by the gypsum. The optional central core wire 355 can also be included to reinforce this structure. Further, wire 355 can be used to precisely position the stent relative to the laser beam during the cutting process in which slits 361, 362 are formed.

The remaining stent structure no longer has any closed electrical loops. It would be difficult, if possible at all, to laser cut the stent in this manner prior to molding it inside the gypsum (or other material), since disconnecting all electrical loops would also result in disconnecting all mechanical structures. To cut through the desired portions 361, 362 of the stent and the outer layer of gypsum, an ultrashort pulsed laser (e.g., in a range of femto-seconds or atto-seconds) can be used in one embodiment. This type of laser is capable of ablating any type of material without significant debris. Because the stent is covered by the gypsum, any debris that does result will settle on the gypsum layer, and not on a stent surface.

Figure 5E:
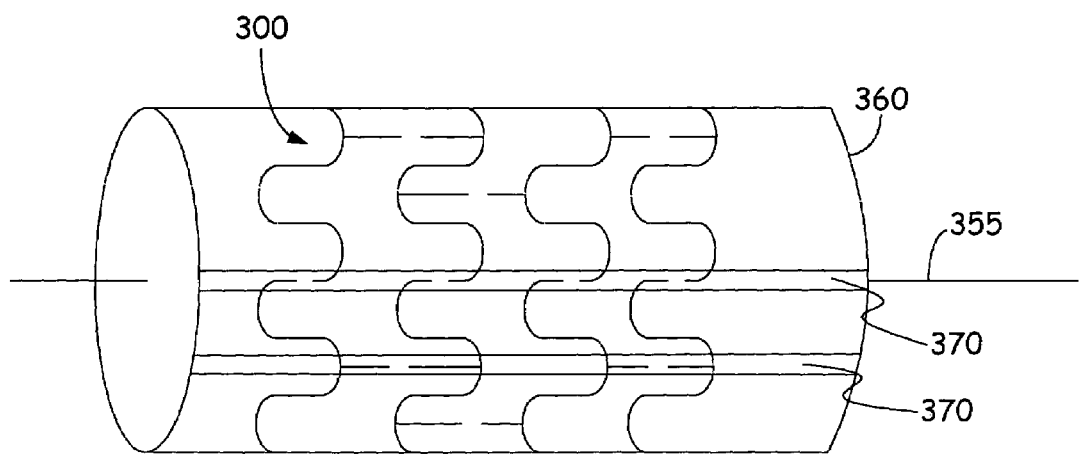

A next step is to fill the cut slits 361, 362 with wax, and to connect all different wax spots to a central wax channel by making small wax lines on the outside of the gypsum rod 360. FIG. 5E illustrate two such wax lines 370 on the outside of the gypsum rod 360. Next, this assembly is covered by a second gypsum layer 380 (shown in FIG. 5F) using any of a variety of techniques. For example, the gypsum rod 360 including wax lines 370 aligned with slits 361, 362 can be again placed in a tube having a slightly larger diameter, providing a structure which would allow the second gypsum layer 380 to harden. Other techniques could be used as well.

Figure 5F:
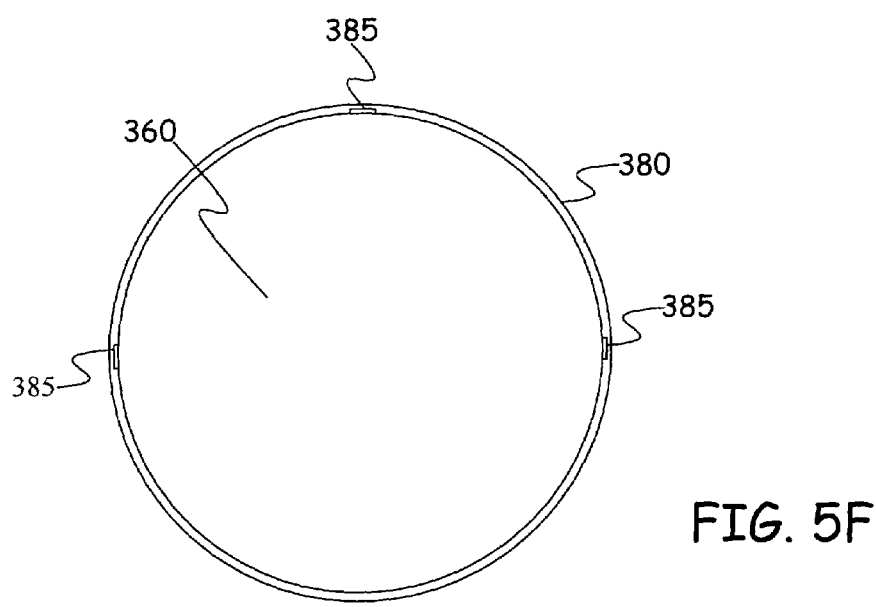

When drying and baking the second layer of gypsum, the wax 370 is removed, leaving open channels 385 (shown in FIG. 5F) where the wax was located. This process is herein referred to as the lost wax method. Although two wax lines 370 are shown in FIG. 5E, and only three open channels 385 are shown in FIG. 5F, those of skill in the art will recognize that such illustration is for purposes of clarity, and that additional wax lines and channels would be formed, corresponding to the various different positions of slits 361, 362 in stent 300.

Figure 5G:
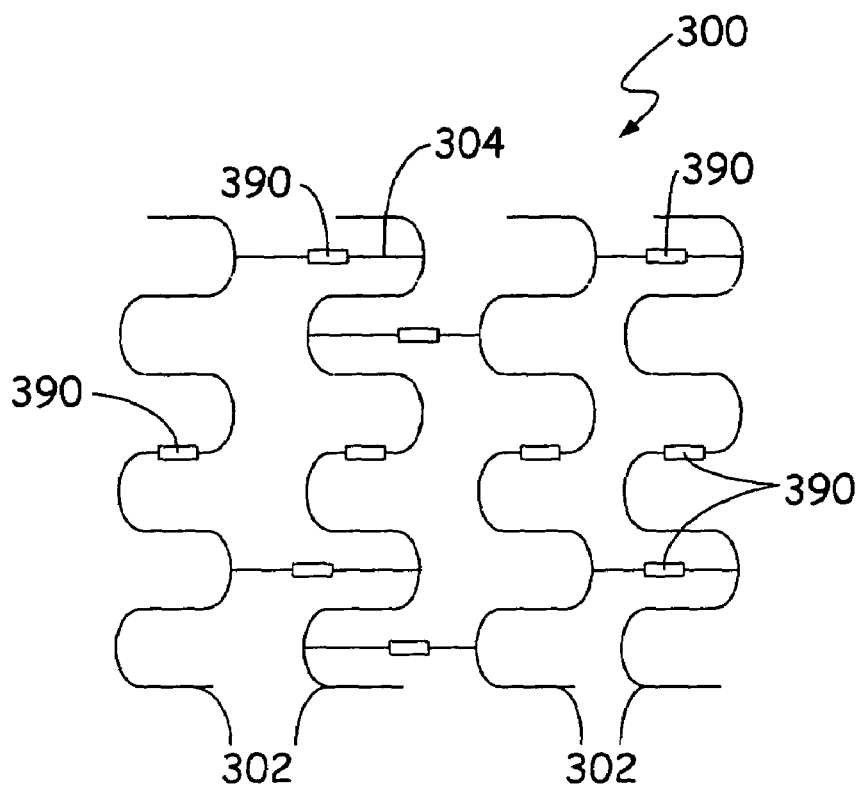
Figure 6A:
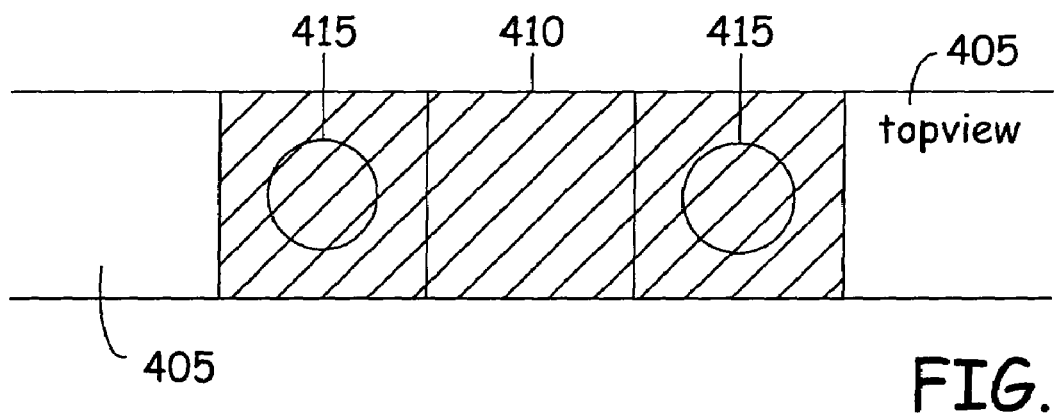
FIGS. 6A and 6B are diagrammatic top and side views, respectively, illustrating one particular embodiment of a ceramic or other non-conducting connector in a stent.
Figure 6B:
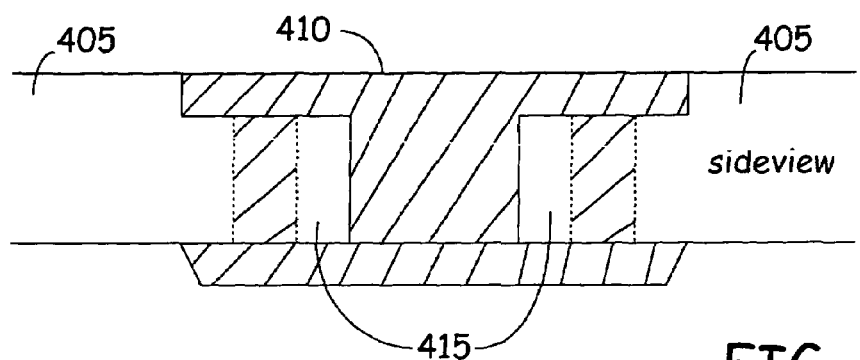

After forming channels 385 using this process, ceramic (for example porcelain) powder material is injected in solution through the lost wax channels 385. The entire assembly is then fired to turn the ceramic fluid into a ceramic structure. After cooling, the gypsum mold, which is very brittle, can be removed. The fine ceramic wires formed in channels 385 are separated. Finally, the ceramic connectors 390 (shown in FIG. 5G) which remain can be polished. It can be worthwhile to use low-firing temperature ceramics, since these are designed to be very polishable. Polishing can be done using normal instrumentation of the type used in dental labs. Any excess gypsum can be removed using a washing, etching or blasting step. The stent can be polished before this process. However, regions to be reconnected may need chemical etching, mechanical blasting or other appropriate surface treatment to increase bond strength. Alternate processing can include starting with a bare tube, placing ceramic connectors or media in a predetermined location or hole and firing or curing the ceramic, and finally laser cutting the stent pattern. This can be done with multi-layer tubes. To provide a robust connection between the metal and the ceramic, special structures can be incorporated in the stent design during the laser cutting of the slits 361, 362. For example, a structure like the one shown in FIGS. 6A (top view) and 6B (side view) representing a ceramic bridge connection in a strut can be used. As used herein, a "strut" refers to a segment of a stent, in a cell segment. FIGS. 6A and 6B illustrate a strut (or other portion) 405 of a stent, for example a portion of a cell or of a connector between cells. Ceramic connector bridge 410 is, for example, one embodiment of ceramic connector bridges 390 shown in FIG. 5G. The cross-hatched areas of connector bridge 410 represent the ceramic material through the strut 405. Two holes 415 have been laser cut. Currently lasercutting capabilities allow holes with diameters as small as 0.0012 inch, and in the near future should allow laser cutting of holes with diameters down to at least 0.0008 inch. In other words, these holes are as little as 10-15% of the average strut width of current stent design.

Figure 7A:
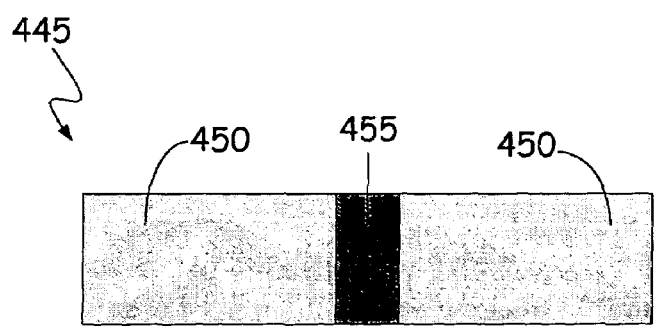
FIG. 7A is a diagrammatic illustration of a metal/ceramic connector which can be used in embodiments of the invention.
Figure 7B:
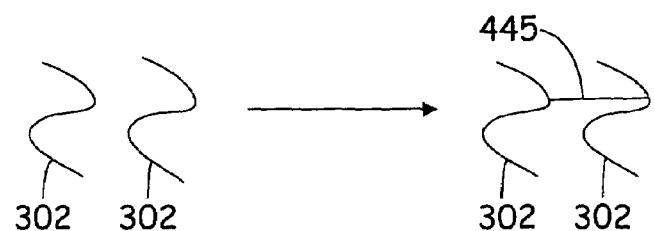
FIG. 7B illustrates portions of two cells or rings of a stent, mechanically separated and mechanically connected, respectively, using a connector such as illustrated in FIG. 7A.

Although a process has been described for obtaining a stent and replacing portions of the stent with electrically non-conductive bridges to eliminate electrical loops formed by the stent, stents having the characteristics of the present invention can be fabricated in other ways. For example, metal/ceramic connectors 445 similar to the one shown in FIG. 7A can be produced. These connectors 445 include metal end portions 450 separated by an electrically non-conductive (ceramic in some examples) material 455. These metal/ceramic connectors 445 can then be welded (or connected by other methods) to a predesigned stent structure. For example, for illustrative purposes, FIG. 7B shows portions of two cells or rings 302 mechanically separated, and then mechanically connected via one of connectors 445.

While ceramic non-conductive materials have been used to describe embodiments thus far, other suitable electrical insulators can be used. For example, any thermoset or thermoplastic polymers, like Teflon, PEO, EPTFE, polyurethane epoxies and acrylics, or other materials can be used, for example, ceramic/polymer composites or nanocomposites. The materials are to be non-conductive to such an extent that they reduce Eddy currents therethrough to a low enough level that it does not result in a significant disturbance in the MRI-generated image in an area where MRI visualization is desired. Of interest is the option to combine different metals in the final stent design and to connect them using the ceramic connectors or bridges. This allows radiopaque sections made out of pure gold, platinum or other materials in those sections of the stent where no mechanical strength is required, and pure titanium or other strong materials in the mechanical backbone section of the stent where strength is required. As described above, in order to eliminate the distortion in MRI, a non-conductive material must be used in the stent in order to eliminate electrical loops. Polymers and ceramics are both materials that fit this criteria. However, polymers can tend to break down over time in the body, where ceramics are typically highly biocompatible and will not break down. An analysis of various ceramic materials, and cements which can be used with the ceramic materials, is provided at the end of this disclose in Appendix A.

Various stent designs are disclosed as solutions to eliminate the problem of induced current in the stent during MRI. In addition to those discussed above, four design types or techniques illustrated in FIGS. 8, 9, 10A-10C and 11A-11C are provided.

Figure 8:
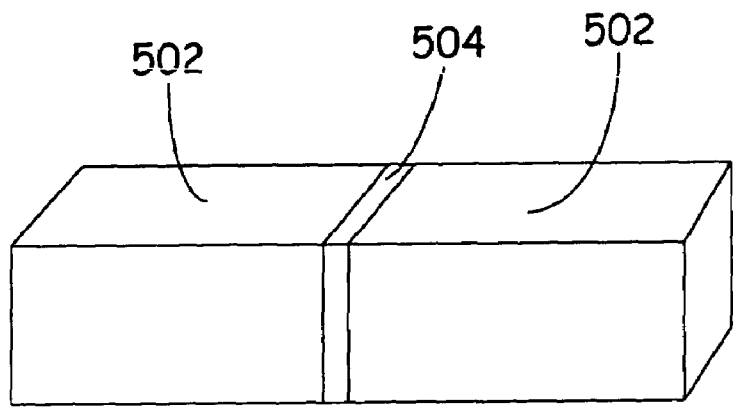
FIG. 8 is a perspective view of a portion of a stent in which first and second metallic portions are connected together and separated by an electrically non-conductive adhesive or cement.

A first design solution to the problem of the formation of electrical loops in the stent is to replace a metallic stent portion with a non-conductive adhesive or cement. This is represented in FIG. 8 in which the metallic portions 502 of a cell or a connector are connected together, and separated by, an electrically non-conductive adhesive, cement or other bonding material 504. The adhesives and cements discussed in Appendix A are examples of materials which can be used to form bonding material 504.

Figure 9:
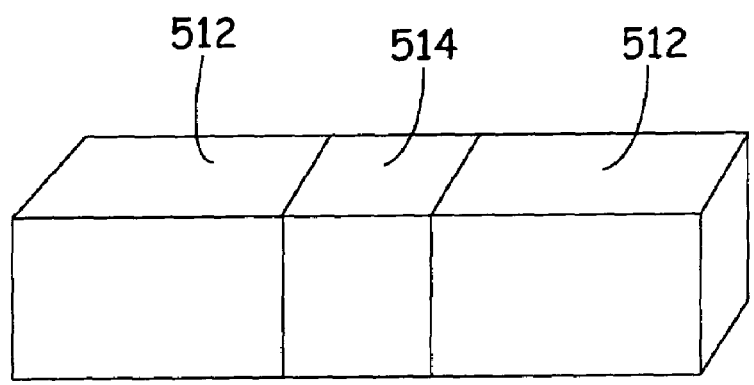
FIG. 9 is a perspective view illustrating a portion of a stent in which first and second metallic stent portions are connected together using a ceramic connector.

FIG. 9 illustrates a second design alternative which can be used to eliminate induced currents in stents during MRI. As illustrated in FIG. 9, this design places a ceramic connector or bridge 514 (which can be, for example, ceramic connectors 390 or 455 discussed above) in-between sections of the cells and/or in-between sections of the connectors which connect the cells. Ceramic bridges 514 can be, for example, cemented or adhered to metallic sections 512. Ceramic bridges 514 can also be fired onto sections 512.

Figure 10A:
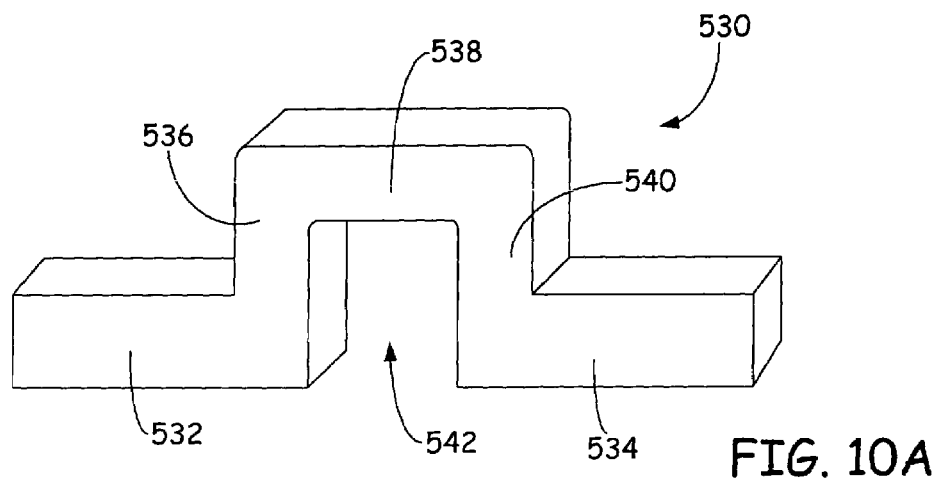
FIGS. 10A-10C are perspective views of a portion of a stent which illustrate a process for forming a ceramic connector between first and second metallic portions of the stent.
Figure 10B:
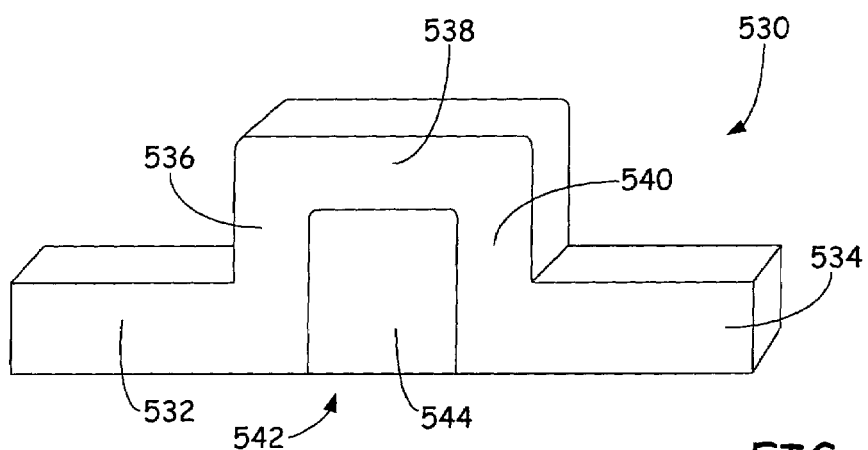
Figure 10C:
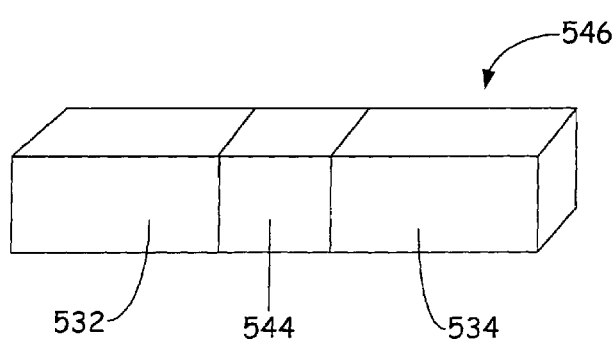

A third type of design, which also includes a ceramic or other electrically non-conductive material positioned between two electrically conductive sections of the stent, can be formed using the process illustrated in FIGS. 10A-10C. Using this technique, as shown in FIG. 10A, an electrically conductive stent portion 530 is provided having first and second sections 532 and 534. Stent sections 532 and 534 are connected by stent sections 536, 538 and 540. Portions of gap 542 extend above the upper surfaces of exist stent sections 532 and 534 (as viewed in FIG. 10A). Next, as illustrated in FIG. 10B, the ceramic or other electrically non-conducting material 544 is formed in gap 542. The ceramic or other material 544 can be attached to stent sections 532, 534, 536, 538 and 540 using any desired technique. For example, for a ceramic material, material 544 can be fired on these stent sections. Once this is completed, a laser cutting process can be used to remove stent sections 536, 538 and 540. The result is a stent structure 546 as shown in FIG. 10C.

Figure 11A:
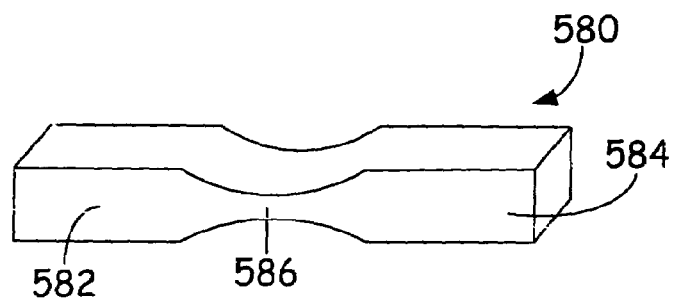
FIGS. 11A-11C are perspective views of a portion of a stent which illustrate an alternate method of forming a ceramic connector between first and second metallic portions of the stent.
Figure 11B:
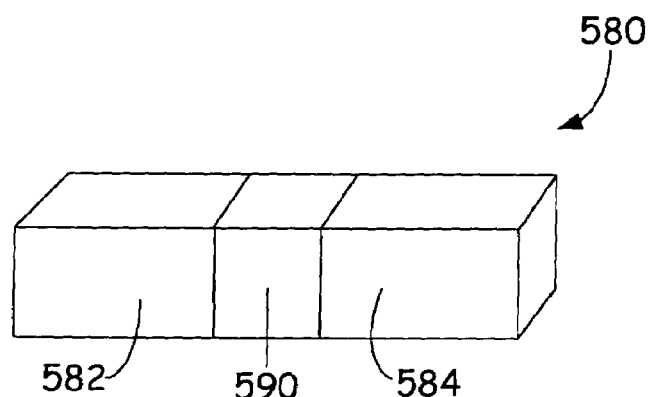
Figure 11C:
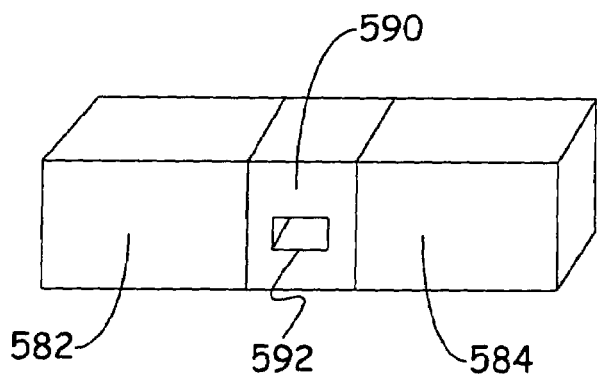

A fourth design or technique is illustrated in FIGS. 11A-11C. As shown in FIG. 11A, using this method an electrically conductive stent portion 580 is provided. Stent portion 580 includes stent sections 582 and 584 having similar dimensions, and being in-plane if desired. Formed in-between stent sections 582 and 584 is a narrowed or tapered stent section 586. Stent section 586 narrows from the dimensions of stent sections 582 and 584 down to dimensions which are smaller than those of sections 582 and 584. Stent portion 580 can be provided, for example, by obtaining a stent portion having substantially constant dimensions between sections 582 and 584, and then laser cutting portions between sections 582 and 584 to form narrowed stent section 586. Narrowed stent section 586 is where the conductive path will be "cut-off", cut out or subsequently insulated in later steps.

Next, as illustrated in FIG. 11B, a ceramic material 590 is fired on over narrowed section 586. In the illustrative embodiment, the ceramic material 590 is formed to have substantially the same outer dimensions as stent sections 582 and 584, but this need not be the case in all embodiments. Finally, a laser (or other techniques) can be used to cut an aperture, hole or tunnel 592 through ceramic material 590. The aperture 592 is aligned such that the process cuts across narrowed section 586 to eliminate the conductive path between sections 582 and 584, and thus eliminating the conductive loop. Aperture 592 can then optionally be refilled with a ceramic material to obtain a structure similar to the one shown in FIG. 10C.

Stents could also be formed from sheets or tubes of metal stock. Beginning with a sheet or a tube of metal stock, one can laser cut only the sections to be joined with insulating bridges. Also indexing notches for future reorientation are cut.

Holes are abated leaving two or more struts to be joined. Illustratively, the holes are large enough to expose the struts while isolating the sides of the holes from contact with ceramic or polymers. This allows the ceramic portion to contact during sintering and cooling without stress while allowing a glaze surface to form, eliminating the need for mechanical polishing.

Once the tube or sheet has all strut holes cut where ceramic bridges are to be made, the strut tips are then encased in a drop of plastic that can be washed away or a bead of wax that can be boiled away. Then the entire tube or sheet is encased in a thin layer of plastic that can "burn out" to create resistive film. The strut tips are then exposed by washing or steaming leaving a negative mold in the burnout plastic. At this point any surface treatments (such as media blasting, acid etching, sputter coating, etc.) can be applied to expose strut tips without damage to the rest.

The ceramic can be applied in several ways, among them 1) dipping, 2) electrophoretic deposition, 3) hot press, and 4) direct application.

Using dipping for example, the previously prepared tube or sheet is dipped into a ceramic slurry (in ultrasonic bath to aid flow). When withdrawn, the plastic resist allows adherence of slurry only in strut holes.

As the liquid portion of the slurry evaporates the deposited particles condense toward the center, pulling away from the resist film on the inside of the strut hole, with a resulting ball encompassing and touching only strut tips. Then, depending on the ceramic selected it would be sintered or infiltrated. In sinters the molten ceramic contracts further and high surface tension tends to pull it into a ball with a smooth surface, (glaze). If infiltrated as with the inceram alumina or inceram zirconia there is no sintering shrinkage and infiltration glass forms a glazed surface.

Electrophoriec ceramic deposition is somewhat analogous to electroforming. In this case exposed strut tips act as the anode and charged ceramic particles collect until a negative mold is filled. This process is currently being used as an extension of the in cerem technique.

Figure 12:
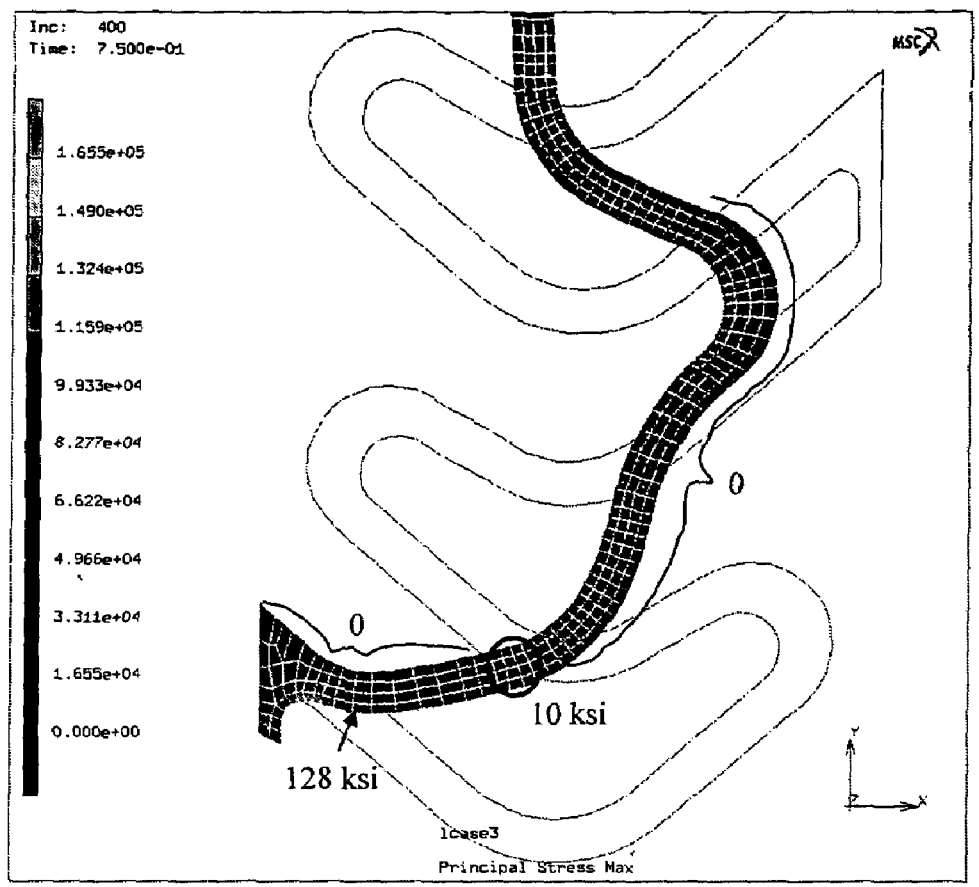
FIG. 12 is a plot illustrating tensile stress, for one particular type of stent, which indicates high and low tensile stress locations when one design embodiment of the stent is fully expanded.

In order for these and other designs to function properly, the non-conductive material must be able to withstand the forces that the stent undergoes during use. For example, some ceramics are known to be very strong in compression, but considerably weaker in tension. FIG. 12 is a plot illustrating tensile stress for one particular type of strut. This plot illustrates where the high and low tensile stresses are located when the stent is fully expanded in one particular example. In this example, a region is located where there is minimum stress, 10 ksi, throughout the width of the strut. A non-conductive material could be placed in this minimum stress area of stent in order to eliminate electrical loops in adjacent metal portions of the stent. Generally speaking, the non-conductive material must have an ultimate tensile stress above the minimum stress for the particular stent in order to avoid failure.

A ceramic that is considered biocompatible is either bioinert or bioactive. A bioinert ceramic provokes minimal response from the host tissue and there is little physical or chemical alteration that takes place in the system. These materials tend to have high wear and corrosion resistance. Alumina, partially stabilized zirconia and silicon nitride, are all bioinert ceramics. Currently, typical applications for bioinert ceramics include bone screws, bone plates, femoral heads and dental restorations. A bioactive ceramic provides a direct chemical bond with tissue and bone. They are surface-reactive ceramics with a low solubility. Hydroxyapatite, calcium phosphate, and bioglasses are all considered bioactive.

As mentioned above, Appendix A provides information on ceramics which have been investigated for potential use in the production of MRI compatible stents. Included are brief descriptions of each of the ceramics: aluminia, glass-ceramic, calcium phosphate, zirconia and silicon nitride. However, the present invention is not limited to use of the particular ceramics described in Appendix A. The material can be a ceramic in a light-curable or catalized material or other materials.

The metal sections can be made out of any non-ferrous metal or metal alloys with a magnetic susceptibility smaller then 1e-05 [cgs/g], such as tantalum, niobium, platinum, gold, titanium, rhenium, palladium or iridium. The non-metallic section can be made out of any non-biodegradable polymer such as polyurethanes, polyethylenes, polyimides, polyamides, polypropylene, polyesters, etc. The non-metallic section can also be made out of a ceramic or ceramic\polymer composition. The structural sections of the stent don't have to be vascular compatible as one can shield the surface with an additional vascular coating such as for example a ceramic layer, by means of for example plasma deposition, or by deposition of a vascular polymer such as for example SIBS (styrene-isobutylene-Styrene).

As discussed above, although various embodiments utilize ceramic materials as the non-conductive connectors or bridges within the stent to eliminate electrical loops, other non-conductive materials can be used as well. For example, in accordance with some embodiments of the invention, after segments of a continuous metal stent strut geometry are cut away, these segments are replaced (via injection molding, coating, adhesive assembly, etc.) with non-conductive elastomers, polymers, or other non-ceramic insulative materials. As in the previously discussed embodiments, this will eliminate conductive path loops in the stent, and thereby reduce the interaction of the stent with the MRI RF energy.

Figure 13A:
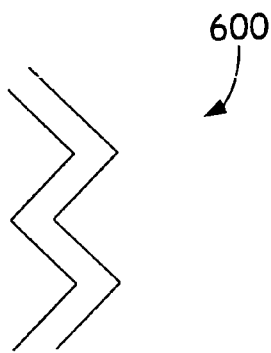
FIGS. 13A-13C are diagrammatic views of a portion of a stent which illustrates an alternate method of eliminating electrical loops in the stent.
Figure 13B:
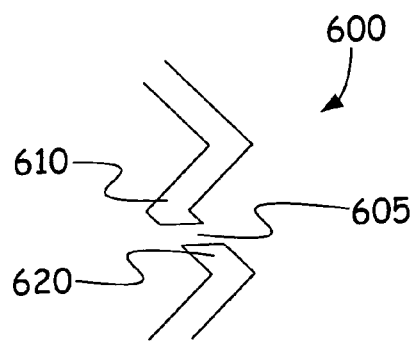
Figure 13C:
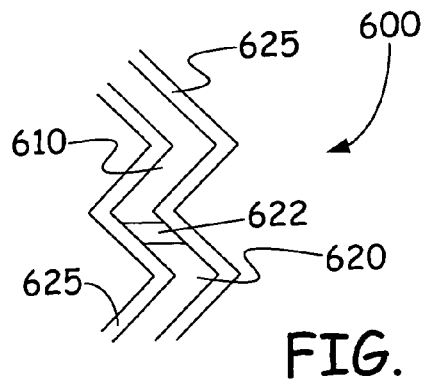

FIGS. 13A-13C illustrate embodiments of the invention which further reduce the occurrence of electrical loops in the stent. FIG. 13A illustrates a portion 600 of a continuous metal stent strut which is to be modified by adding a non-conductive connector or bridge. As shown in FIG. 13B, a segment 605 of the metal stent strut is cut away, for example using a laser cutting process, leaving metal end sections 610 and 620. If necessary, the stent can be mechanically supported during the process of removing section 605 using a variety of techniques, including for example the technique illustrated in FIGS. 5A-5G.

Then, as illustrated in FIG. 13C, a non-conductive material or bridge 622 is formed between metallic end sections 610 and 620. Non-conductive material 622 can be, for example, elastomer material, polymer material, ceramic material, or other insulative materials, and can be formed using a variety of techniques such as those described above. As discussed previously, this reduces conductive path loops in the stent to thereby reduce the interaction of the stent with the MRI RF energy.

However, if the insulative segments 622 are found to be electrically bridged by conductive paths between the stent metal end sections 610 and 620 and body tissue or fluids, further enhancements can be made to the stent. For example, as illustrated in FIG. 13C, the metal stent 600 is coated with a biocompatible, insulative covering or coating 625. Examples of materials that can be used for the insulative segments 622 and coating 625 are polyethylene oxide (PEO), Polyetheretherketone (PEEK) or other appropriate oxide layer.

As described in previous embodiments, one way to reduce or eliminate the artifacts in MRI by non-ferrous metal stents is to make hybrid (metal-ceramic) structures avoiding any electrical closed loops. As was proposed, the production process can start by taking a finished metal stent, laser cutting slots in the stent to disconnect the struts. By filing these slots with a ceramic, one can re-establish the stent structure. While the previously described technique can be effective, other less labor intensive techniques of producing stents, without electrical loops, are also disclosed.

To build further upon the earlier disclosed idea of producing a MRI compatible stent out of nonferrous metals and ceramics, the idea is to start with making all the loose metal components out of flat metal pieces by a stamping or cutting or metal injection molding process. In other words, instead of dividing a stent in a number of separate elements as was the result of making slots in a finished stent, the idea is to make these separate elements directly out of base material. The parts can subsequently be bent to the required stent radius. However the bending and cutting of the parts can actually also be done in a combined processing step by forcing the metal plate in a preshaped curved die. A very suitable process for this stamping/bending operation would be to use a magnetic pulse system. these systems are known and magnetic pulse system is described for example at website http://www.pulsar.co.il/technology/advantages.htm. The advantage of using a magnetic pulse system being high precision (1 micrometer) and high repeatability of the process, as well as this being a cold process. Of course, conventional stamping would also be applicable. Another process which can be used to form these parts out of flat plates is photo etching.

Using (UV-curing) adhesives, in combination with micro assembly technologies of the type used in microelectromechanical systems (MEMS) fabrication, stents can be constructed out of these stent-kits. For example the precision micro assembling kit made by Sandia laboratories (http://www.sandia.gov/isrc/Capabilities/Prototyping/Precision Miscro Assembly/precision micro assembly.html) can be used.

Further, ceramic or polymer inlets can be added in addition to just gluing the elements together. This allows the creation of electric capacitors in the stent design. In case of using doped polymers (carbon fibers or other fillers), conducting polymers, or conducting ceramics, resistors can be created in addition to capacitors. Polyaniline or polyAcetylene polypyrolle doped with $I_2$ are examples of conducting polymers. Table 1 shown below shows the conductance of some potential ceramics, but of course there are many more available.

TABLE 1

| | Thermal conductivity [W · m − 1 · K − 1] | Electrical conductivity [W · cm] |
|---|---|---|
| Al2O3 | 20 | 1012 |
| BN | 33 | 2 · 1013 |
| MoSi2 | 50 | 21.6 · 10−6 |
| SiC | 90 | ~2 |
| Si3N4 | 15-20 | 1013 |
| TiC | 10 | 65-85 · 10−6 |
| TiN | 20 | 0.11 · 10−4 |
| Y2O3 | 18 | >108 |
| ZrB2 | 60 | 9.7 · 10−6 107-108 at 20° C. |

The combination of capacitors, resistors and the inherit presence of a coil structure (the stent structure) would allow the creation of LRC circuits in the stent with resonant frequencies equal to the Larmor frequency. The addition of the resistors would allow designs to influence the quality factor Q of the circuit, and by that the width of the resonant peak, in order to compensate for a frequency mismatch between the resonant frequency and the Larmor frequency. This mismatch is highly likely to occur as the self-inductance of the stent coil geometry is independent of the geometry of the stent after deployment. Therefore, it may be better to work with lower Q-factors in order to more easily compensate for any mismatch.

$$Q=1/(\omega_0 \cdot C \cdot R)$$

In embodiments in which LRC circuits are to be created in the stent, when using adhesives to connect the ceramic or polymer inlets to the metal stent structure, electrically conducting adhesives can be used, or care can be taken to make sure that part of the metal structure is in direct contact with the inlet or electrical contact is made after the inlet is glued.

Finally in relation to the electric circuits, in order to provide an outside electrical isolating layer, the entire stent is coated with a polymer or ceramic non-conducting coating. Plasma ion immersion implantation (PIII) processes can be used in obtaining coverage of the stent with the isolating ceramic layer. Plasma deposition can create the isolating layer. An electric isolating layer prevents conductance through the surrounding blood and tissue which could short-circuit the ceramic/polymer inlets.

Since parts of many shapes can be made out of most metals and alloy, stents can be made out of multiple metals, for example highly radiopaque metals like Platinum or Gold near a distal or proximal edge, and very flexible alloys like Nitinol or strong alloys like Titanium at structurally essential locations. The separation of the metal elements by ceramics, as well as the complete enclosure of the whole stent by a ceramic layer or other layer, will prevent corrosion caused by galvanic reactions between the different metals. In other words, hybrid ceramic-metal stents with coatings allow the use of any number of metals which might not ordinarily be used together.

Using stent-kits as described allows any shape of stent to be built. Besides building the usual round stents, non-circular, tapered, side-branched or multi-layer stents can be fabricated. For example one could build a bifurcation stent using a stent-kit. This technology could also be used to make septal defect closure devices.

Figure 14:
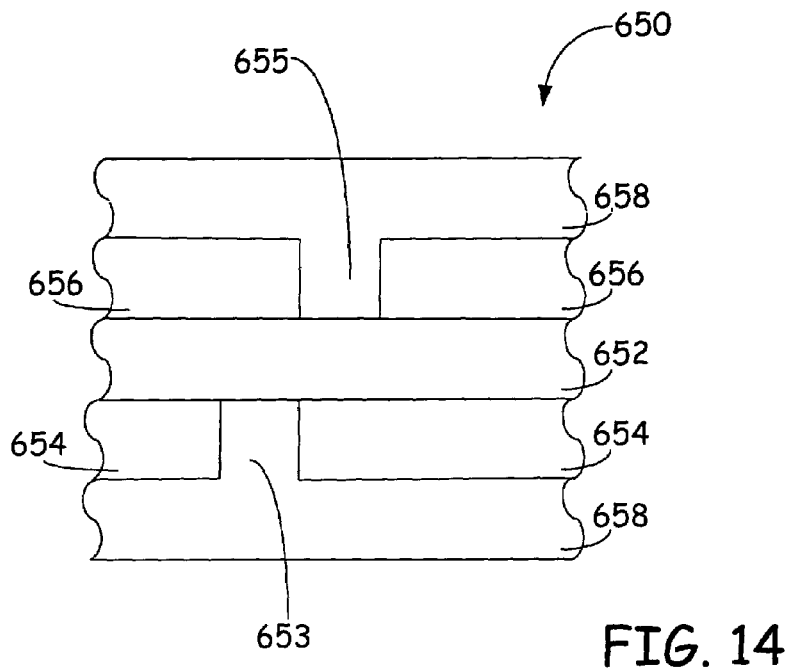
FIG. 14 is a diagrammatic side view of a portion of a stent illustrating a structure which eliminates electrical loops in an alternate embodiment.

FIG. 14 is a diagrammatic side view illustration of a portion of a stent 650 in accordance with yet another embodiment of the present invention. While various embodiments of the present invention have been shown which include ceramic or other non-conducting materials used to electrically isolate first and second metallic end sections of the stent, while at the same time structurally supporting the stent to some degree, layered metal/ceramic structures can be used as well. Layered structures of, for example, metal/ceramic/metal are known, as are methods of manufacturing such layered structures. Such a layered structure will not reduce the occurrence of RF artifacts during MRI if the metal layers of the structure are allowed to form closed loops. However, if discontinuities are formed in the metal layers, but not in the ceramic layer, this process can be used to eliminate electrical loops, and thereby the occurrence of RF artifacts.

As shown in FIG. 14, stent portion 650 is formed from a layered structure which includes metal layers 654 and 656 on either side of ceramic layer 652. Fine slits 653 and 655 are made, respectively, in outer metal layers 654 and 656 in order to eliminate electrical loops formed by either of these layers. Although for illustrative purposes slits 653 and 655 are shown in close proximity to each other, this need not be the case. To maximize the strength of the strut, slits 653 and 655 can be made in different portions of the stent (for example in different portions of a particular cell or connector) or in other non-overlapping configurations such that at any specific location the stent includes at least the ceramic layer and one of metal layers 654 and 656. Slits 653 and 655 can be made, for example, using a UV-ablation laser or an ultrashort pulsed laser. If the entire surface of the stent (or at least the regions surrounding any slit) is coated with an isolating oxide layer 658, then there is little or no risk of current bridging across the slits using surrounding blood or tissue.

Figure 15:
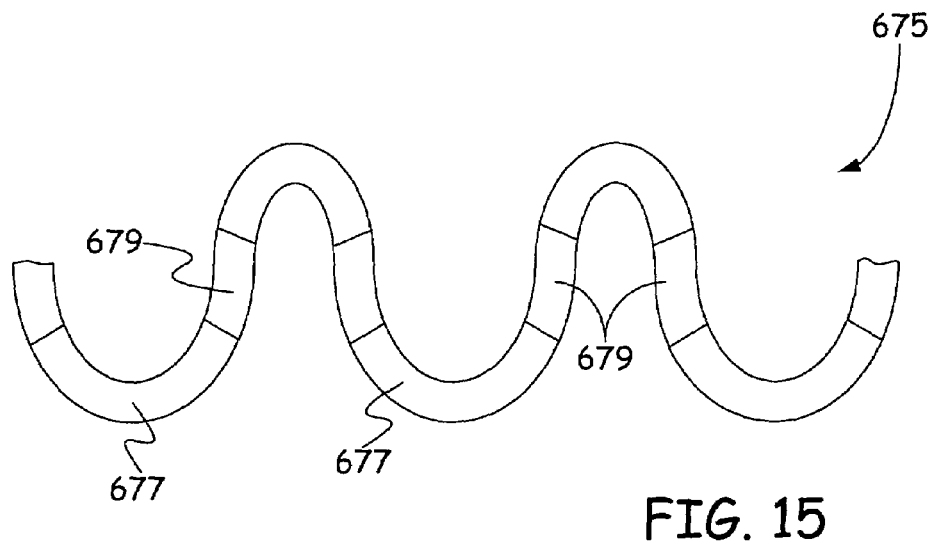
FIG. 15 is a diagrammatic side view of a portion of a stent illustrating alternating metal sections and non-conducting connector sections.

Shown in FIG. 15 is a portion of a stent 675 which demonstrates various concepts of the present invention described above. For example, as described above with reference to the graph shown in FIG. 12, stent 675 can be made using high strength metals in one or more regions 677 determined to be high stress regions of the stent, while electrically non-conductive materials can be used in one or more regions 679 determined to be low stress regions in order to eliminate electrical loops while maintaining sufficient structural strength of the stent. In the alternative, low magnetic susceptibility material, such as Titanium, can be placed in the low stress regions 679, while higher magnetic susceptibility materials such as Tantalum can be placed in regions 677 where more strength is required. In this manner, total magnetic susceptibility of the stent can be reduced without negatively impacting its mechanical performance.

Consistent with the above discussions, current stainless steel and nitinol stents have been found to be less than ideally compatible with MRI and MRA imaging, because the magnetic susceptibility of the metal alloys is sufficiently high relative to human tissues and creates a disturbance in the magnetic field of the scanner, and because the continuous metal loops in the stent geometry have induced currents leading to RF shielding. As a result, the area within the stent lumen and area adjacent to the stent often have signal void that prevents diagnostic or procedural imaging there.

In this disclosure approaches to building a passive MRI compatible stent have been described. These approaches can be summarized as using a stent metal material with significantly low magnetic susceptibility, and designing a structure that does not have closed conductive loops. The challenge is that structures without interconnections are not as strong and stiff as structures with connections. This approach could lead to stents with compromised mechanical properties and scaffolding in order to gain MRI compatibility.

Figure 16:
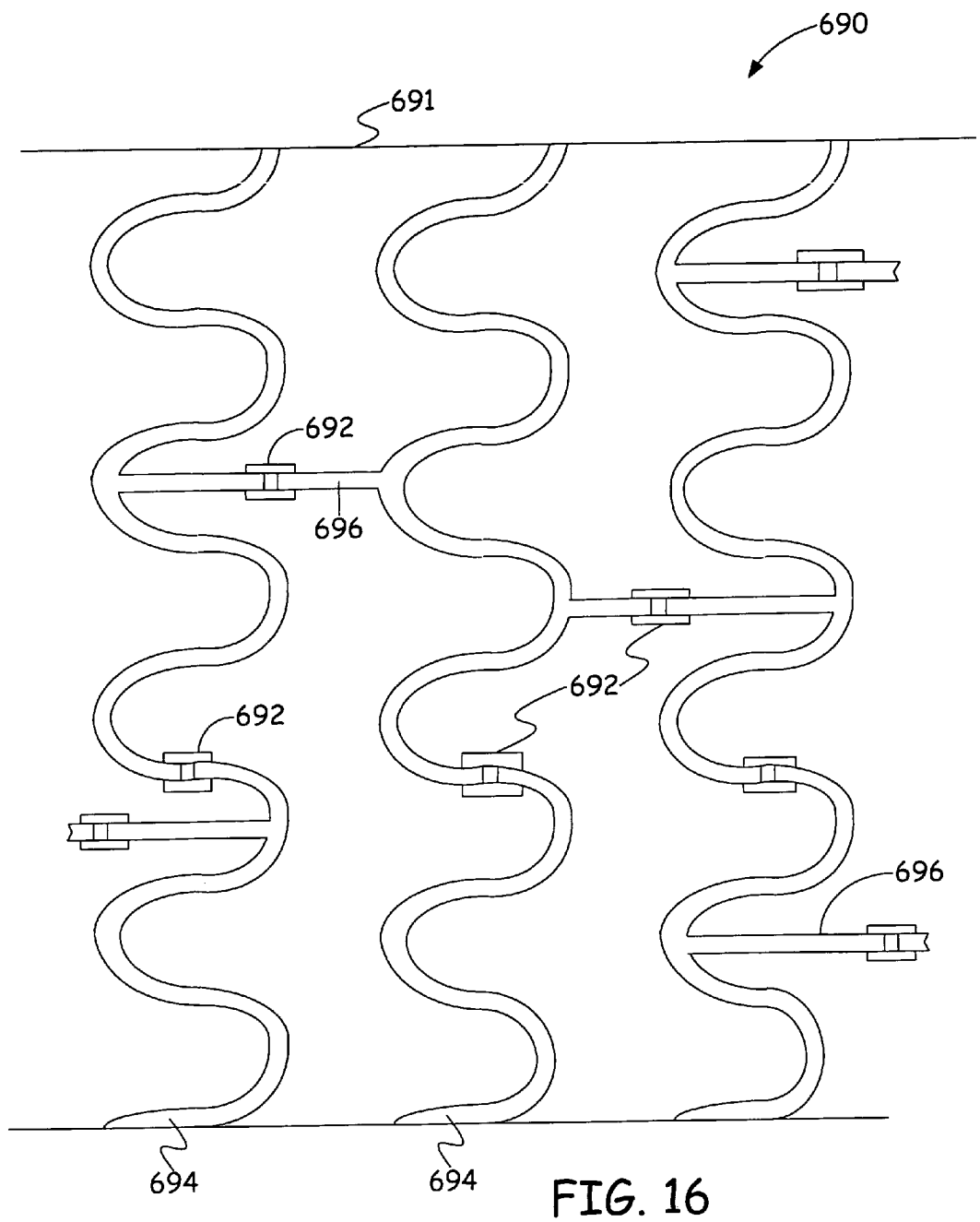
FIG. 16 is a diagrammatic side view of a portion of a metallic stent including a plurality of electrically non-conducting connectors, in accordance with various embodiments of the present invention, in order to eliminate electrical loops formed in the stent.

A disclosed technique for making such a stent is to create metal discontinuities by laser or mechanical cutting, and to attach the ends of the discontinuities with insulative fasteners. Generally, a stent 690 of this type is shown in FIG. 16 with ceramic bridges (or other electrical discontinuities) 692 formed in each cell 694 and in each connector 696. The stent is shown engaged in a lumen 691. Beyond use of pure ceramics and pure polymers, re-enforcement layers can be used as well.

Although the present invention has been described with reference to illustrative embodiments, workers skilled in the art will recognize that changes may be made in form and detail without departing from the spirit and scope of the invention.

APPENDIX A

The focus of this project is to develop a MRI compatible stent. Currently, stents are not compatible because they cause an artifact (distortion) in the image. Blood flow through the stent along with the tissue surrounding the stent can not be seen as a result of these artifacts. There are two main factors associated with the stents that cause artifacts in the MRI: the magnetic susceptibility of the implant material and the interference caused by the Faraday effect. MRI functions by assuming a uniform magnetic field, so when there are materials present with high differences in magnetic susceptibilities the image becomes distorted. In order to reduce these factors, materials with low magnetic susceptibilities (as close to water and human tissue as possible) must be used. The second reason for distortion can be explained with Faraday's Law. When a coil of wire (in this case a stent) is placed in a changing magnetic field a current is induced. This current interferes with the field from the magnet and results in a distortion. Eliminating these conductive path loops in the stent will reduce the interference with the MRI. One way of accomplishing this is to use a nonconductive material in portions of the stent to "cut-off" any conductive paths. Ceramics have been the focus due to their high biocompatibility. The ceramic would have to be bond on to the stent with an adhesive, fired-on or some other technique.

This report contains a brief description of the different designs that are currently being considered to eliminate the artifacts. The stress tests that have been conducted on a stent are discussed. Research was conducted on the different ceramics and cements that could be used Data that was obtained from different suppliers is included in this report. The tests that have been conducted and are being conducted to test the bonding strength of different cements are also discussed.

MELTING TEMPERATURES OF CERAMICS AND METALS

| Material | Melting Temp, °C. (°F.) |
|---|---|
| Alumina | 2050 (3722) |
| Zirconia | 2681-2847 (4857.8-5156.6) |
| Silicon Nitride | 1926 (2200) |
| Titanium | 1668 |
| Tantalum | 2200-2996 |

Aluminum Oxides

The most common form of aluminum oxides used is polycrystalline $\alpha$-$Al_2O_3$. As the grain size of these decreases the strength increases. Alumina products can be purchased with purities anywhere from 80-99.9%. Typically, as the purity increases so does the strength. Alumina with a content greater than 99.5% has excellent corrosion and wear resistance. However, the more pure the alumina the more expensive the product is as well. The alumina can also be strengthened by adding zirconia (Zirconia Toughened Alumina, ZTA). Alumina devices used in the medical field are produced from high purity alumina that is sintered and pressed at temperatures between 1600-1700° C. This material is commonly used in joint replacement because of its hardness and excellent wear resistance. It can also be used in dental restorations. Problems with this material include its brittle nature along with difficulty in fabrication. There are some alumina products that are specifically designed to be easily machined. One way to increase the machinability is to produce porous alumina; however, these products-usually sacrifice strength for machinability.

PROPERTIES OF CERAMICS

| Material | Density, g/cc | Modulus of Elasticity, GPa (psi * $10^6$) | Flexural Strength, MPa (ksi) | Compressive Yield Strength, MPa (ksi) | Ultimate Tensile Strength, MPa (ksi) | Fracture Toughness, MPa-$m^{1/2}$ |
|---|---|---|---|---|---|---|
| 80-85% Alumina | 3.45-3.5 | 215-240 (31.2-34.8) | 205-310 (29.7-45) | 965-2760 (140-400) | 103-138 (15-20) | |
| 90-95.5% Alumina | 3.55-3.96 | 300 (43.5) | 276-345 (40-50) | 2068-2586 (300-375) | 138-193 (20-28) | 3.5-4.5 |
| 96-98% Alumina | 3.67-3.96 | 300-355 (43.5-51.5) | 296-375 (42-54) | 2068-2586 (300-375) | 131-205 (19-29.7) | 3.5-5.0 |
| 99-99.5% Alumina | 3.83-3.89 | 375 (54.4) | 310-379 (45-55) | 2550-2600 (370-377) | 172 (25) | 4-4.5 |
| 99.5% Alumina | 3.75-3.97 | 375-393 (54.4-57) | 345-482 (50-70) | 2068-3650 (300-530) | 138-220 (20-32) | 4-5 |
| Alumina, ZTA | 4.0 | 360 (52.2) | 450 (65.3) | 2900 (421) | | 5-6 |
| Zirconium oxide 99.9% (Zr/Hf/Y) | | 210 (30.5) | 1000 (145) | 2000 (290) | 7 (1.02) | 10 |
| Glass Ceramic | 2.52 | 66.9 (9.7) | 94 (13.6) | 345 (50) | | 1.53 |
| Zirconia, TTZ | 5.7 | 200 (29) | 620 (89.9) | 1750 (254) | | 11 |
| Zirconia, FSZ | 6.0 | 200 (29) | 900 (131) | 2500 (363) | | 13 |
| Zirconia, PSZMg | 5.7 | 200 (29) | 620 (89.9) | | | 11 |
| Zirconia, PSZYt | 6.0 | 200 (29) | 850 (123) | | | 8 |
| Silicon nitride, Reaction sintered | | 96-220 (13.9-31.9) | | 520 (75.4) | 68-172 (9.86-24.9) | |
| Silicon nitride, hot pressed | 3.31 | 317 (46) | 679-896 (98.5-130) | 689-2760 (99.9-400) | 360-434 (52.2-62.9) | 5.0-8.0 |

ZTA—Zirconia Toughened Alumina
TTZ—Transformation Toughened Zirconia
FSZ—Fully Stabilized Zirconia
PSZMg—Partially Stabilized Zirconia with Magnesium
PSZYt—Partially Stabilized Zirconia with Yttrium Suppliers Associated Ceramics and Technology, Inc. has alumina available ranging from 80-99.9%. The following table indicates the different properties of these products. The company can machine the products into different shapes upon request.

TABLE 1

ASSOCIATED CERAMICS AND TECHNOLOGY, INC. ALUMINA PRODUCTS PROPERTIES

| Product | Alumina Content, % | Density, g/cc | Flexural Strength, MPa (ksi) | Compressive Strength, MPa (ksi) | Tensile Strength, MPa (ksi) |
|---|---|---|---|---|---|
| ACT 800-850 | 80-85 | 3.45-3.5 | 241-276 (35-40) | 1793 (260) | 103-138 (14.9-20) |
| ACT 900, 920, 960 | 90-96 | 3.55-3.75 | 276-345 (40-50) | >2068 (>300) | 138-193 (20-28) |
| ACT 990, 997, 999 | >99.5 | 3.75-3.96 | 345-379 (50-55) | >2068 (>300) | 138-172 (20-24.9) |

MarkeTech International Inc. also has a selection of alumina products available. The typical properties for their products are shown below.

TABLE 2

MARKETECH INC. ALUMINA PRODUCTS PROPERTIES

| Product | Alumina Content, % | Density, g/cc | Elastic Modulus, GPa (psi * $10^6$) | Flexural Strength, MPa (ksi) | Tensile Strength, MPa (ksi) | Fracture Toughness, (MPa-m$^{1/2}$) |
|---|---|---|---|---|---|---|
| 960P | 96.0 | 3.67 | 300 (43.5) | 375 (54.4) | 205 (29.7) | 4-5 |
| 975P | 97.5 | 3.75 | 355 (51.5) | 375 (54.4) | 205 (29.7) | 4-5 |
| 995P | 99.7 | 3.96 | 375 (54.4) | 410 (59.5) | 220 (31.9) | 4-5 |
| ZTA | 80.0 | 4.1 | 340 (49.3) | 450 (65.3) | — | 7 |

Astro Met Inc. produces several forms of alumina. This company manufactures 2 different aluminum oxides: AmAlOx 68 and AmAlOx 87. AmAlOx 68 is 99.8% aluminum oxide and has been developed for maximum wear and corrosion resistance. This material has a high density, high hardness, fine grain structure, and excellent mechanical strength. AmAlOx 87 has a higher purity for applications, which require a pure material along with a high density, high strength, and small grain size. The small grain size allows for tight tolerances. This product was originally developed for critical load bearing medical implants. ZTA-96 is a zirconia-toughened alumina, composed of 85% alumina and 15% zirconia. This product combines wear resistance property from AmAlOx 68 with high strength and toughness of AmZirOx 86. Properties for all of these products are shown in Table 3.

TABLE 3

ASTRO MET, INC. ALUMINA PRODUCTS PROPERTIES

| Product | Density, g/cc | Grain Size, μm | Modulus of Elasticity, GPa (psi * $10^6$) | Flexural Strength, MPa (ksi) | Fracture Toughness, MPa-m$^{1/2}$ |
|---|---|---|---|---|---|
| AMALOX 68 99.8% Alumina | 3.93 | 4 | 393 (57) | 382 (55.4) | 5 |
| AMALOX 87 99.95% Alumina | 3.97 | 2 | — | 482 (69.9) | — |
| ZTA-96 85% Alumina 15% Zirconia | 4.1 | 1.5 | 310 (45) | 760 (110) | 6 |

Superior Technical Ceramics Corp. supplies 5 different dense alumina products ranging from 95-99.8%. The following table lists the properties of these products. The company produces different sizes in both plate and rod form.

TABLE 4

SUPERIOR TECHNICAL CERAMICS CORP. ALUMINA PRODUCTS PROPERTIES

| Alumina Content, % | Flexural Strength, MPa (ksi) | Compressive Strength, MPa (ksi) | Tensile Strength, MPa (ksi) |
|---|---|---|---|
| 95 | 283 (41) | 2206 (320) | 138 (20) |
| 96 | 310 (45) | 2068 (300) | 131 (19) |
| 98 | 296 (43) | 2413 (350) | 152 (22) |
| 99.5 | 310 (45) | 2586 (375) | 173 (25) |
| 99.8 | 310 (45) | 2586 (375) | 172 (25) |

Cotronics focuses on machinable ceramics. The company produces an aluminum silicate (Rescor 902) and a 96% alumina (Rescor 960) which can both be machined with standard shop equipment. All of Cotronics' products can be purchased in rods or plates. The properties of these two products are shown in Table 5.

TABLE 5

COTRONICS ALUMINA AND ALUMINA SILICATE PROPERTIES

| Product | Density, g/cc | Flexural Strength, MPa (ksi) | Compressive Strength, MPa (ksi) |
|---|---|---|---|
| Rescor 902 - Aluminum Silicate | 1.92 | 96.5 (14) | 262 (38) |

TABLE 5-continued

COTRONICS ALUMINA AND ALUMINA SILICATE PROPERTIES

| Product | Density, g/cc | Flexural Strength, MPa (ksi) | Compressive Strength, MPa (ksi) |
|---|---|---|---|
| Rescor 960 - 96% Alumina | 3.8 | 262 (38) | 414 (60) |

Accuratus Ceramic Corp. produces three grades of alumina (94, 96, 99.5%) all in the alpha phase. The company can fabricate the ceramic to a specific design need. Table 6 shows the properties for these ceramics.

TABLE 6

ACCURATUS CERAMIC CORP ALUMINA PRODUCTS PROPERTIES

| Alumina Content, % | Density, g/cc | Modulus of Elasticity, GPa (psi * $10^6$) | Shear Modulus, GPa (psi * $10^6$) | Flexural Strength, MPa (ksi) | Compressive Strength, MPa (ksi) | Fracture Toughness, MPa-m$^{1/2}$ |
|---|---|---|---|---|---|---|
| 94 | 3.69 | 300 (43.5) | 124 (18) | 330 (47.9) | 2100 (305) | 3.5 |
| 96 | 3.72 | 300 (43.5) | 124 (18) | 345 (50) | 2100 (305) | 3.5 |
| 99.5 | 3.89 | 375 (54.4) | 152 (22) | 379 (55) | 2600 (377) | 4 |

International Ceramic Engineering (ICE) manufactures and fabricates different ceramics, including four different alumina materials (94, 96, 99.5, 99.8%). The company specializes in post-fire machining and tight tolerance grinding. All different shapes can be fabricated including custom designed ones. A zirconia toughened alumina is also available. The properties for ICE's alumina products are shown in Table 7.

TABLE 7

INTERNATIONAL CERAMIC ENGINEERING ALUMINA PRODUCTS PROPERTIES

| Alumina Content, % | Density, g/cc | Flexural Strength, MPa (ksi) | Compressive Strength, MPa (ksi) | Tensile Strength, MPa (ksi) | Fracture Toughness, MPa-m$^{1/2}$ |
|---|---|---|---|---|---|
| 94 | 3.96 | 310 (45) | 2586 (375) | 172 (25) | 4.5 |
| 96 | 3.96 | 310 (45) | 2586 (375) | 172 (25) | 4.5 |
| 99.5 | 3.85 | 310 (45) | 2586 (375) | 172 (25) | 4.5 |
| 99.8 | 3.92 | 296 (43) | 2413 (350) | 152 (22) | 4.5 |
| ZTA | — | 450 (65.3) | 2900 (421) | — | 5-6 |

Glass-Ceramics

Glass-ceramics typically have high tensile strength and high resistance to abrasion. However, the downfall with this type of material is that it is very brittle and can not be used in a load-bearing operation. This polycrystalline material is formed by controlling the crystallization of glasses. The grain size of glass-ceramic is smaller than conventional ceramics. The tensile strength is typically between 100-200 MPa (14.5-29 ksi). It has a resistance to abrasion and scratching similar to sapphire. The fatigue behavior may be better than that of conventional ceramics.

Suppliers

Corning produces Macor, which is a machinable glass-ceramic with good physical properties, no porosity, and is electrically insulating. Macor is composed of 55% fluorophlogopite mica and 45% borosilicate glass (weight percent of compounds shown below). The randomly ordered mica flakes allows the material to be machined. This product can be joined to other materials in a variety of ways. Brazing has been used to join Macor to different kinds of metals, an epoxy can be used, sealing glass produces a tight seal and a mechanical joint can be made. The material can be machined using diamond, silicon carbide or aluminum oxide grinding wheels. The properties of Macor are shown below.

TABLE 8

MACOR MACHINABLE GLASS CERAMIC COMPOSITION

| | Silicon $SiO_2$ | Magnesium MgO | Aluminum $Al_2O_3$ | Potassium K | Boron $B_2O_3$ | Fluorine F |
|---|---|---|---|---|---|---|
| Composition, wt % | 46 | 17 | 16 | 10 | 7 | 4 |

TABLE 9

MACOR MACHINABLE GLASS CERAMIC PROPERTIES

| | Density, g/cc | Modulus of Elasticity, GPa (psi * 10⁶) | Shear Modulus, GPa (psi * 10⁶) | Flexural Strength, MPa (ksi) | Compressive Strength, MPa (ksi) | Fracture Toughness, MPa-m$^{1/2}$ |
|---|---|---|---|---|---|---|
| Macor | 2.52 | 66.9 (9.7) | 25.5 (3.7) | 94 (13.6) | 345 (50) | 1.53 |

Cotronics, Astro Met Inc., Accuratus and International Ceramic Engineering all supply Macor. The product can be purchased in rods or plates. Both Accuratus and ICE will custom design the glass-ceramic to fit the customers needs.

Bioglass (USBiomaterials, Alachua, Fla.) and Ceravital (E. Leitz Wetzlar GmBh; Wetzlar, Germany) are bioactive glasses that have been successful in clinical tests. The following two tables list the composition and the mechanical properties of these two bioactive glasses.

TABLE 10

BIOGLASS AND CERAVITAL COMPOSITIONS

| Composition, wt % | $SiO_2$ | NaO | CaO | $P_2O_5$ | MgO | $K_2O$ |
|---|---|---|---|---|---|---|
| Bioglass | 45 | 24.5 | 24.5 | 6.0 | — | — |
| Ceravital | 40-50 | 5-10 | 30-35 | 10-15 | 2.5-5.0 | 0.5-3.0 |

TABLE 11

BIOGLASS AND CERAVITAL PROPERTIES

| Properties | Elastic Modulus, GPa (psi * 10⁶) | Compressive Strength, MPa (ksi) |
|---|---|---|
| Bioglass | 35 (5.08) | 42 (6.09) |
| Ceravital | 100-150 (14.5-21.8) | 500 (72.5) |

Further information on suppliers of these two products was not found.

Zirconia

The crystal structure of zirconia at room temperature is monoclinic, which has excellent dielectric, piezoelectric, and ion-conductive properties. By adding dopants this structure can be stabilized and transformed into the tetragonal crystal structure (Partially Stabilized Zirconia—PSZ). Zirconia has a high chemical resistance, a high fracture toughness ($K_{IC}$), high bending strength, and a high hardness. Unlike other ceramics, a crystal transformation (tetragonal to monoclinic) and volume expansion (3-5%) can take place at the appearance of a high-tension region. The volume expansion causes wedges in the cracks thus slowing down the continuation of the crack. The elastic modulus for all forms of zirconia range from 190-230 GPa (27.6*10⁶-33.4*10⁶ psi). The flexural strength and fracture toughness varies with the form and the grain size. The material is usually formed by adding a dopant and then the composition is hot pressed. The melting temperature of zirconia ranges from 2681-2847° C. (4857.8-5156.6° F.), which is too high for this ceramic to be fired onto a metal. Current typical applications for zirconia are for femoral heads, artificial knees, bone screws and plates and dental restorations[2]. Zirconia has excellent wear resistance and higher fracture toughness and stiffness than alumina. It is commonly only used when alumina does not have high enough strength due to the high cost.

Suppliers

Astro Met Inc. produces AmZirOx 86, a yttria stabilized zirconia (Yttria Tetragonal Zirconia Polycrystal, Y-TZP). The product's high strength and toughness allow this material to function well in applications where wear, corrosion, impact and abrasion are factors. The product undergoes transformation toughening which allows for it to withstand impact forces that most ceramics can not. Table 12 gives the properties of this zirconia product.

TABLE 12

ASTRO MET, INC. ZIRCONIA PROPERTIES

| Product | Density, g/cc | Grain Size, μm | Modulus of Elasticity, GPa (psi * 10⁶) | Flexural Strength, MPa (ksi) | Fracture Toughness, MPa-m$^{1/2}$ |
|---|---|---|---|---|---|
| AmZirOx 86 95% Zirconia 5% Yttria | 6.01 | 0.5 | 204 (29.6) | 1000 (145) | 7 |

Vesuvius McDanel produces a yttria stabilized zirconia ceramic (Z105) with a composition as shown below.

TABLE 13

VESUVIUS MCDANEL ZIRCONIA CERAMIC COMPOSITION

| Compound | Wt % | Compound | Wt % |
|---|---|---|---|
| Zirconia ($ZrO_2$) | 88.84 | CALCIA (CAO) | 0.1 |
| Yttria ($Y_2O_3$) | 10.5 | MAGNESIA (MGO) | 0.01 |
| Silica ($SiO_2$) | 0.2 | Sodium Oxide ($Na_2O$) | 0.006 |
| Alumina ($Al_2O_3$) | 0.17 | Potassium Oxide ($K_2O$) | 0.002 |
| Titania ($TiO_2$) | 0.14 | | |

This product has the following properties:

TABLE 14

VESUVIUS MCDANEL ZIRCONIA PROPERTIES

| Product | Density, g/cc | Flexural Strength, MPa (ksi) | Compressive Strength, MPa (ksi) |
|---|---|---|---|
| Zirconia (Z105) | 5.72 | 276 (40) | >1772 (257) |

International Ceramic Engineering has two forms of zirconia available for purchase: transformation-toughened zirconia (TTZ) and yttria-stabilized zirconia polycrystals (YTZP). The properties for these zirconia products are shown in Table 15.

TABLE 15

INTERNATIONAL CERAMIC ENGINEERING ZIRCONIA PROPERTIES

| Zirconia Form | Modulus of Elasticity, GPa (psi * $10^6$) | Flexural Strength, MPa (ksi) | Compressive Strength, MPa (ksi) | Fracture Toughness, MPa-m$^{1/2}$ |
|---|---|---|---|---|
| TTZ | 200 (29) | 620 (89.9) | 1750 (254) | 11 |
| YTZP | 200 (29) | 900 (130.5) | 2500 (363) | 13 |

Calcium Phosphate

Calcium phosphate based ceramics are commonly researched as a possible material for hip replacements and dental implants due to the capability of the ceramic to sustain bone cell growth. Hydroxylapatite (HA), $Ca_{10}(PO_4)_6(OH)_2$, resembles the primary inorganic component of bone, and is currently used to coat metal joint implants for better cementation. Typical calcium phosphate polycrystalline hydroxyapatite values are as follows: elastic modulus=40-117 GPa ($5.8*10^6$-$17*10^6$ psi), flexural strength=147 MPa (21.3 ksi) and density=3.16 g/cc. Dense calcium phosphate has tensile strengths ranging from 40-200 MPa (5.8-29 ksi) and compressive strengths of 120-900 MPa (17.4-130.5 ksi)[5].

Suppliers

Spire Corporation produces SPI-Ceramic™, which is a film that can be applied to ceramics, metals, or polymers. This ceramic film is used in the medical area to improve the mechanical and biological properties of the devices. Applications for this product include: orthodontic appliances, dental implants, blood collection and monitoring devices, needles and needle guidewires, orthodontic implants, and spinal screws. This film is beneficial because it improves the blood compatibility and is corrosion resistive. Mechanically, it improves the wear resistance and hardness of the devices.

Silicon Nitride

This particular material is known for its high strength, hardness and fracture toughness. Silicon nitride compounds can withstand high structural loads (even at high temperatures) and it has excellent wear resistance.

Suppliers

Rauschert Industries Inc. produces several different varieties of ceramics including silicon nitride. Properties for this material are shown below.

TABLE 16

RAUSCHERT INDUSTRIES INC SILICON NITRIDE PROPERTIES

| | Density, g/cc | Modulus of Elasticity GPa, (psi * $10^6$) | Flexural Strength, MPa (ksi) | Compressive Strength, MPa (ksi) | Fracture Toughness, MPa-m$^{1/2}$ |
|---|---|---|---|---|---|
| Silicon Nitride | 3.23 | 290 (42) | 800 (116) | >2500 (363) | 7 |

International Ceramic Engineering produces a silicon nitride that is lightweight and has good thermal characteristics. The properties of this silicon nitride product are shown in the following table.

TABLE 17

INTERNATIONAL CERAMIC ENGINEERING SILICON NITRIDE PROPERTIES

| | Density, g/cc | Flexural Strength, MPa (ksi) | Fracture Toughness, MPa-m$^{1/2}$ |
|---|---|---|---|
| Silicon Nitride | 2.50 | 345 (50) | 3.0 |

Feldspathic Porcelain

In dentistry, leucite reinforced feldspathic porcelain is commonly used. This ceramic typically contains about 60% $SiO_2$, 20% $Al_2O_3$, and various amounts of $Na_2O$ and $K_2O$ for expansion control. Porcelain can be slurry formed or hot pressed and has flexural strengths ranging from 60-165 MPa. The formation of leucite crystals strengthens the material by inhibiting micro crack propagation. These crystals also control the thermal expansion. Porcelain can be strengthened through fusion to a higher CTE, which leads to residual compressive stress that limits crack formation. In order to counter Griffith's flaws, compression can be induced on the surface through ion exchange of potassium atoms for sodium atoms. Manufacturers claim that this process increases the tensile strength by 53%. Tuf Coat GC International, Tokyo, Japan and university tests confirm these results. Duceram low fusing ceramic from Degussa, Germany was the lowest temperature material at 640.6° C. (1185° F.) that was found.

Materials and Methods

The first step in producing porcelain fused to metal crown is to take an impression from the mouth to make an analog of the tooth from artificial stone. Next, a thin layer of metal in the shape of a thimble is made to adapt intimately to the cut-tooth-structure. The metal is usually formed through the lost wax casting method, but cad-cam, electroforming, and foil and sintered metal can also be used. The purpose of this is to produce a 300 micron or thinner substructure (coping) which the layers of shaded porcelain can be stacked. Gold, platinum, palladium, silver, nickel, chrome, cobalt and titanium are all metals that can be used for the substructures. Trace elements are added to these for grain refinement and oxide formation. The formation of metal oxides into a molten ceramic opaque layer creates a strong covalent bond between the metal and ceramic. For materials, such as gold, that are non-oxidizing a bonding agent (powdered metal and ceramic frit) is used. To mask the metal and develop color, a layer of opaque porcelain is fired on the surface. In small increments the powder/liquid slurry is used to build up the anatomic shape (plus the shrinkage of the material) of the tooth. The powder is allowed to dry in a vacuum chamber and then heated at 100° F. per minute from 950° F. to 1680° F. The shape is corrected and the surface textured refined. The crown is fired in air to form a surface glaze.

Titanium is an attractive choice for a substructure because of its biocompatibility and low cost. Porcelain systems have been developed with lower firing temperatures in order to avoid structural damage to the titanium. These systems have lower thermal expansions to match the CTE of titanium. To avoid oxidation at the metal ceramic interface methods such as, argon purge, bonding paste, electroplating and sputter coating are used. A test was devised to determine whether these techniques could be applied to produce an electrically insulating, biocompatible, strong bond to metal. Details about these tests can be seen in the test section.

Other Ceramics

Stronger ceramics have been developed to improve the optical properties and eliminate the need for metal reinforcement. John McClean added alumina crystals to porcelain (aluminous porcelain) to blunt microcracks. This material was stronger, but too opaque for dental applications. Dentsply marketed Corning's Macor under the name Dicor. Although test data looked promising, survival in the mouth proved poor and the product was removed from the market. Empress (Ivoclar, N.A Amherst, N.Y.) is a hot pressed Leucite reinforced feldspathic porcelain. Empress II is a lithium-disilicate glass framework that is layered with flourapatite based veneering porcelain. This material has a flexural strength of 350 MPa. Inceram alumina from Vita Zahnfabrik in Bad Sakingen, Germany is a mesh of lightly sintered alumina that has been infiltrated with glass and veneered with porcelain. Three point bending tests indicated a flexural strength of 446 MPa. Inceram zirconia (Vita Zahnfabrik) is similar to Inceram alumina only with 35% partially stabilized zirconia, which increases the flexural strength to 800 MPa. Procera from Noble Biocare (Gotborg, Sweden) is a densely sintered high purity aluminum oxide with veneered framework and feldspathic porcelain. The flexural strength of Procera is 600 MPa. Cercon, a yttria-stabilized tetragonal zirconia from Dentsply Ceramco (York, Pa.) has a flexural strength of 900 MPa. Partially sintered blocks are milled and fully sintered at high temperatures [5000° F. (2760° C.)] for several hours. The fired samples shrink 20-30%.

Conclusion

While all the ceramics listed are biocompatible and all have the potential to withstand the required forces, an alumina or zirconia product would most likely be the best ceramic for a ceramic to adhere to metal. Alumina and zirconia have high strengths along with high corrosion and wear resistance. Zirconia is stronger than alumina and at smaller sizes the machinability is better. However, due to the high cost of zirconia, alumina should be chosen if it functions appropriately for this application. Another option is the zirconia toughened alumina which adds strength to the alumina, yet is not as expensive as zirconia. If the ceramic is going to be fired on the stent as opposed to cemented then the melting temperature of the ceramic compared to the metal used will be crucial. The ceramic must melt at a low enough temperature to not effect the structure of the metal. Silicon nitride has a considerably low melting temperature for a ceramic; however, this material does not have as high of strength as zirconia or alumina.

Cements

This section lists some of the common cements that are currently being used in the medical field. These cements are used for both ceramic and metallic bonding. This report focuses on the cements that are being used in the dentistry area, because it is an area where biocompatible cements are commonly used. It was assumed that if the cement has been deemed orally biocompatible it is likely that it will function throughout the rest of the body, although further testing would have to be done to assure this assumption.

This report gives a brief description of each of the cements; zinc phosphate, glass ionomer, resin reinforced glass ionomer, polycarboxylate, cyanoacrylates, and resin composites. After each of the descriptions there are some suppliers listed and a more detailed description of their particular product. References to the web sites where this information and further information can be obtained are given in the footnotes.

TABLE 1

CEMENT PROPERTIES

| Cement | Supplier | Product | Diametric Tensile Strength MPa (ksi) | Ultimate Compressive Strength MPa (ksi) | Elastic Modulus GPa (ksi) |
|---|---|---|---|---|---|
| Zinc Phosphate | (general data) | (general data) | 5-7 (0.725-1.015) | 80-110 (11.6-15.95) | 13 (1885) |
| | Ormco | Zinc Phosphate | 5.52 (0.800) | 75.8 (11.0) | |
| | Ormco | Protech Gold | 11.7 (1.697) | 96.5 (14.0) | |
| Glass Ionomer | (general data) | (general data) | | 90-230 (13.05-33.36) | |
| | Pulpdent | GlassCore | | 179 (25.96) | |
| | Pulpdent | GlassBase | | 227 (32.92) | |
| | 3 M | Ketac-Cem | | 141 ± 14 (20.45 ± 2) | |
| | 3 M | Ketac-Molar | | 230 (33.36) | |
| | 3 M | Vitremer Luting | 23.2 (3.365) | 132.5 (19.2) | |
| RRGI | 3 M | Vitrebond | | | |
| | Bisco | Illusion | 45 (6.527) | 300 (43.51) | 6 (870) |
| | Bisco | C&B | 43 (6.237) | 235 (34.08) | 7.2 (1044) |
| Resin | 3 M | Relyx ARC | 65 (9.427) [LC] | 340 (49.31) [LC] | |
| | | | 60 (8.702) [SC] | 325 (47.13) [SC] | |
| | J. Morita | Bistite II DC | 42 (6.091) | 348 (50.47) | |
| | J. Morita | M-Bond | N/A | N/A | |

RRGI—Resin Reinforced Glass Ionomer
LC—Light Cure
SC—Self Cure

TABLE 2

CEMENT PROPERTIES

| Cement | Supplier | Product | Bond Strength/ Adhesion MPa (psi) | Solubility ($H_2O$ %) | Fracture Toughness (MPa-m$^{1/2}$) | Flexural Strength MPa (ksi) |
|---|---|---|---|---|---|---|
| Zinc Phosphate | (general data) | (general data) | — | 2 | — | — |
| | Ormco | Zinc Phosphate | Enamel: <0.689 (100) SS: 0 | 0.5 | — | — |
| | Ormco | Protech Gold | Enamel: 4.14 (600) SS: 0.689 (100) | — | — | — |
| Glass Ionomer | (general data) | (general data) | — | — | — | — |
| | Pulpdent | GlassCore | — | — | — | — |
| | Pulpdent | GlassBase | | 0.17 | 0.33 | |
| | 3M | Ketac-Cem | — | — | — | 15 ± 5 (2.18 ± 0.7) |
| | 3M | Ketac-Molar | — | — | 0.78 | 33 (4.79) |
| | 3M | Vitremer Luting | — | — | — | — |
| RRGI | 3M | Vitrebond | — | — | — | — |
| | Bisco | Illusion | — | — | — | 100 (14.5) |
| | Bisco | C&B | — | — | — | 113 (16.4) |
| Resin | 3M | RelyX ARC | — | — | — | |
| | J. Morita | Bistite II DC | Co—Cr alloy: 22.8 (3306) Au—Pd alloy: 22.9 (3321) | — | — | 98 |
| | J. Morita | M-Bond | — | — | — | 56 |

*No fatigue data available from the companies
*No shrink rate or shrinkage available
*No electrical conductivity data Zinc Phosphate General Description This type of cement is typically hard and rigid and it bonds through mechanical means. Currently, the cement is used in the dentistry area for well-fitting posts, crowns, metal inlays, and aluminous all-ceramic crowns. The typical material specifications are as follows: compressive strength 80-110 MPa (11.60-15.95 ksi), tensile strength 5-7 MPa (725-1015 psi), and modulus of elasticity 13 GPa (1.89*10$^6$ psi). One of the disadvantages to this kind of cement is that the setting time is often slow. The cement is gradually soluble in oral fluids and can be an irritation to pulp. Zinc phosphate cement is becoming obsolete in the dentistry area due to these complications.

Suppliers

Two suppliers were found for zinc phosphate cements, Mizzy, Inc. and Masel. Little information regarding these suppliers with regard to this cement was found. Masel was contacted about further information, but there has been no response.

Glass Ionomer (GI)

General Description

There are many types of glass ionomer cements on the market that are used for dentistry work. These cements typically bond to the tooth structure through ionic means. The compressive strength generally ranges from 90-230 MPa (13.05-33.36 ksi). The elastic modulus is lower resulting in the material being susceptible to elastic deformation in high stress regions[2]. They are fairly inexpensive, but typically have a low resistance to mechanical wear.

In general this kind of cement is technique-sensitive. In one study comparing glass ionomer to composites, it was determined that the failure rate for the glass ionomer was much higher. This is probably due to the fact the cement requires little moisture exposure for the first 24 hours, which is difficult in a clinical setting. Tests were not done on light-cured glass ionomers, which have a faster setting time.

Suppliers

Pulpdent sells six different kinds of glass ionomer cements along with a few other types of cements. All of their GI cements have a fluoride ion release and are acid-etchable. The cements have a low thermal expansion coefficient (9-ppm). The bond strength is high along with fairly high compressive and diametric tensile strengths. Two of Pulpdent's GI cements that may be applicable to use in this study are the GlassCore™ and the GlassBase™. The compressive strength for the GlassCore™ is 179 MPa (26,000 psi) and for the GlassBase™ 227 MPa (33,000 psi).

Process Description

GlassCore

Pulpdent Bond Conditioner must first be applied to all dentin and metal surfaces for 10 seconds. The powder portion and liquid portion are mixed together for about 20 seconds. The working time for this cement is 3 minutes and the initial setting time is 6 minutes from the finish of mixing.

GlassBase

Once again a Pulpdent Bond Conditioner is applied to the surfaces and depending on the application a light cure bonding resin may need to be added and cured. The mixing, working time, and setting time are the same as with GlassCore™. A light cure bonding resin may be applied to the cement and to etched surfaces afterwards.

Ketac-Cem, Ketac-Molar, and Vitremer Luting Cement are glass ionomer cements from 3M. Ketac-Cem's powder portion is composed of glass powder, polycarboxylic acid, and pigments. The liquid portion is water, tartaric acid, and conservation agents. This luting cement is used for the cementation of inlays, onlays, bridges, and crowns with metal or ceramics and composite veneering. The solubility in the oral environment is quite low with this cement. The compressive and flexural strengths are high and it has a good resistance to mechanical wear. The opacity is high at 230% (relative to aluminum) and the biocompatibility is considered acceptable. Ketac-Molar is a metal-free glass ionomer that is designed as a filling material in the teeth, so the mechanical properties and its radiopacity (260%-relative to aluminum) are higher than Ketac-Cem. The compressive strength of this material is 230 MPa (33.36 ksi) and it has a flexural strength of 33 MPa (4786 ksi). Vitremer Luting Cement contains a powder and a liquid portion. Fluoroaluminosilicate glass containing a microencapsulated potassium persulfate, an ascorbic acid catalyst, and small amounts of an opacifying agent make up the powder portion of this cement. The liquid portion is a solution of polycarboxylic acid modified with pendant methacrylate groups, HEMA, water, and minimal amount of tartaric acid. Vitremer Luting Cement's applications include: luting metal inlays, onlays or crowns, cementation of porcelain fused-to-metal crowns, pre-fabricated and cast post cementation, and luting orthodontic appliances. This product does not have any measurable solubility like most GI cements. The fracture toughness of this cement is higher than other GI products as well.

Process Description

Ketac-Cem

All enamel, dentin and metal surfaces must be cleaned and dried before cement can be used. Dentin can not be exposed to the cement directly so the surface must be coated with a calcium hydroxide preparation. The powder and liquid portions are then mixed together for about 30 seconds. The working time is 3 minutes and the setting takes place in 7 minutes from start of mixing.

Ketac-Molar

No information on instructions for use of this product.

Vitremer Luting Cement

The surfaces of the inlays, onlays or crowns must all be thoroughly cleaned before the procedure. The pulp needs to be protected as with the Ketac-Cem. The powder and liquid portions are mixed together for 30 seconds. Once mixing is completed the cement has a working time of 2.5 minutes and then after placement setting will occur in 3 minutes. This product does not have to be light cured.

Dentsply-Sankin makes a glass ionomer cement that can be used as both a luting and a base cement. The product claims to have excellent biocompatibility and a compressive strength up to 190 MPa (27.56 ksi). No further information about properties or process description was received from the company.

Resin Reinforced Glass Ionomer (RRGI)

General Description

Resin reinforced glass ionomer cements (or resin-modified) have higher strengths (both compressive and tensile) and a lower solubility than regular glass ionomers. Their adhesion properties are similar to glass ionomers. There is some concern with using this product for cementing posts due to a possible expansion-induced fracture[2].

Suppliers 3M has a resin modified glass ionomer (RMGI) liner/base material called Vitrebond. The recommended use for this material is as a liner or base under metal, ceramic, composite, and amalgam restorations. The powder component is composed of $SiO_2$, $AlF_3$, ZnO, SrO, cyrolite, $NH_4F$, MgO, and $P_2O_5$, which are all fused together. The powder is radiopaque. A modified polyacrylic acid with pendant methacrylate groups, HEMA, water, and photoinitiator make up the liquid component. Both components are light sensitive. Unlike many GI cements, the Vitrebond sets with a brief exposure to light. The compressive strength is 96.5 MPa (14.0 ksi), diametrical tensile strength is 17.4 MPa (2.52 ksi), and the flexural strength is 25.5 MPa (3.70 ksi). The radiopacity of this material is 1.6 (relative to aluminum). Vitrebond has passed cytotoxicity, mucosal irritation, primary skin irritation, and Magnussan-Klingman sensitization tests. It is not recommended for direct pulp capping.

Process Description

Vitrebond

The powder and liquid portions are mixed together. Since the product is light cured, setting does not occur until light exposure so the working time is flexible and setting occurs immediately when the user is ready.

GC America, Inc. makes a few reinforced glass ionomer cements. GC FujiCEM is recommended for the final cementation of resin crowns, metal, porcelain fused to metal, bridges, inlays, and ceramic inlays. The preparation for this material takes very little time. This cement has two paste components as opposed to the typical powder/liquid combination. The film thickness is very low in comparison with glass ionomer cements and other resin reinforced cements. Clinically, this cement is insoluble once it is set, which reduces the chance of microleakage or washout. The material is considered biocompatible and radiopaque. GC Fuji PLUS bonds both chemically and mechanically to all types of core materials. This cement can be used for final cementation of metal or porcelain fused to metal bridges, crowns, inlays, or onlays. The product claims to have excellent bond strength and to be clinically insoluble. GC Fuji ORTHO comes in either a light-cure (LC) or self-cure (SC) cement. The ORTHO LC is used to bond metal, porcelain and polycarbonate brackets and metal bands to enamel. This product has a low sensitivity to moisture. ORTHO LC can be purchased in capsules or as a powder-liquid component. ORTHO SC bonds brackets, bands, and acrylic appliances. With both of these products the technique is simplified, no etch is required, and the success rate is high.

Process Description

GC FujiCEM

The two pastes are mixed together in 10 seconds either by hand or with a Paste Pak Dispenser. There is a 3-minute working time and 1.5 minutes after this for removal of cement before setting.

GC Fuji PLUS

Optionally, Fuji PLUS Conditioner can be used on the bonding surface to increase the bond strength and reduce chance of pulp irritation. The cement is then applied within the working time of 2.5 minutes. Any excess cement must be removed within 30 seconds before final setting occurs.

GC Fuji Ortho LC and SC

No instructions available at this time.

Bisco, Inc. produces Illusion™ for cementation of porcelain and composite veneers, crowns, inlays, onlays, and metallic crowns, inlays, and onlays. The composition of Illusion™ is 15-30% Ethoxylated Bisphenol-A-dimethacrylate, 60-70% glass filler and 5-12% Triethyleneglycol dimethacrylate. C&B Opaque is also made by Bisco and is commonly used for metal crowns, inlays, onlays and restorations. The cement catalyst portion is composed of three ingredients: 30-60% silica, 30-60% Bisphenol-A-diglycidylmethacrylate and 5-15% Triethyleneglycoldimethacrylate. The cement base is composed of 8-30% Bisphenol-A-diglycidylmethacrylate, 8-30% Ethoxylated Bisphenol-A-dimethacrylate, 15-40% silica, 15-40% glass frit and less than 1% sodium fluoride.

Process Description

Illusion

The process varies depending on what kind of cementation is done. With metal restorations, the surface should be sandblasted for 1-2 seconds and then rinsed with water and air-dried. Two coats of ONE-STEP adhesive should be applied to the surface.

The Base and Catalyst Pastes should be mixed together and placed on the appropriate surface.

C&B Opaque

The metal surface should be sandblasted before beginning. An adhesive, like ONE-STEP or ALL-BOND 2 should be applied before cementation. The working time for this product is 3 minutes and the setting time is 4.5 minutes.

Polycarboxylate Cement

General Description

This type of cement is used in the dentistry area because it adheres chemically to the tooth through an interaction of free carboxylic acid groups with calcium. The compressive strength (55-85 MPa; 7.98-12.33 ksi) is generally lower than that of the zinc phosphate cements. However, the tensile strength is higher (8-12 MPa; 1.16-1.74 ksi) and the plastic deformation is greater with the polycarboxylate cements. This cement has been proven to be biocompatible with dental pulp. The recommendation for this cement is for single metal units in a low stress area with short span prostheses.

Suppliers

L.D. Caulk produces Tylok Plus, an anhydrous polycarboxylate cement, so only water is needed for mixing. Currently, it is used for final cementation of crowns, bridges, and inlays. It could also be used as a base or cavity liner under restorative materials. This material is biocompatible against the pulp and bonds ionically to the enamel and dentin. The minimum compressive strength for the luting cement is 60 MPa (8.70 ksi) and for a base cement, 70 MPa (10.15 ksi). However, according to the MSDS on this material, irritation may occur to the soft tissue in the body, so this product may not be applicable for use in a stent.

Process Description

Tylok Plus

The powder is mixed with water for 30 seconds. The minimum working time is 1 min 45 seconds and the maximum setting time is 7 minutes.

Composites

General Description

Composite restorative materials are typically BIS_GMA/TEGMDA resins filled with silanated silica or zirconia, barium glass for radiopacity, colorants to match teeth photo-initiators and chemical catalysts. Smaller cavities can be filled directly, usually light cured, then shaped and polished. Indirect restorations (lab produced) undergo further polymerization utilizing heat, pressure, inert gas and various light sources. Composite Supreme from 3M contains agglomerated nano-filler with a tensile strength of 90 MPa. Bisco Inc. makes the indirect lab composite Tescera atl with a tensile strength of 64 MPa. Other lab composites include Sinfony by 3M ESPE (St. Paul, Minn.) and Belleglas by Kerr Sybron (Romuhus, N.Y.). Sculpture by Pentron lab Technologies LLP is BIS-GMA free, utilizing polycarbonate di-methacrylate (PCDMA) and ethoxylated biphenyl A di-methacrylate (EBPADMA) as the resin.

Process Description

To make inlays, onlays and crowns of composites, an analog of the prepared tooth is made of artificial stone from a mold taken from the mouth. Material is packaged in a light-proof syringe. Small increments are carried on the tip of the instrument and adapted to prep the analog and then short bursts of light hold them in place. Polymerization of surface is inhibited by atmospheric oxygen thus allowing a complete bond to subsequent layers. When the form is complete, the restoration can be fully cured using light, heat, vacuum or an inert gas. For high stress applications (molars, bridges, etc), high strength fibers are incorporated. Ribbond brand (Seattle, Wash.) is made of Spectra from Allied Signal (Honeywell). These fibers are plasma treated to allow a chemical bond to resins. The modulus of elasticity is 24,000 ksi (165.5 GPa) and the tensile strength is 3.51 GPa (509 ksi). One idea to increase the tensile strength would be to stitch prongs together with high strength fiber. A bundle of fiber drawn through the restoration is fully cured using light, heat, vacuum or an inert gas in cure the oxygen inhibited layer. A hole in the prong could be anchored and encased with polymer. Or prongs with a serrated profile could be coated with resin cement for insulation and then placed together side by side, wrapped with fibers and then encased in a drop of polymer.

Color Shade Effect on Strength

While dental material suppliers want to make strong composite systems, optical properties to match teeth must be considered. Adding opacifiers, pigments, fluorescent agents, and adjusting filler loading can lead to translucence. Studies show that strength varies with shade and translucency. If the formula is adjusted for maximum strength disregarding appearance, the physical properties should be improved.

Cyanoacrylates

General Description

Cyanoacrylates are commonly used, as super glue. Polymerization occurs by a rapid anionic mechanism with the aid of a weak base like water. The bond formed with cyanoacrylates is very strong. One downfall with this type of cement is that in some cases they have been found to be carcinogenic. Methyl cyanoacrylate causes an acute inflammatory response as a result of formaldehyde that is left behind. Currently, n-butyl cyanoacrylate and 2-octylcyanoacrylate have been approved for use in the United States. This material is mainly used for soft tissue adhesion, like treating lacerations.

Suppliers

There were no suppliers found for cyanoacrylates cements that are currently used in the medical field.

Resin Composite Cements

General Description

This type of cement typically combines filled Bisphenol-A-glycidyldimethacrylate (BIS-GMA) resin with different methacrylics. Polymerization can occur through photopolymerization, chemical mechanisms, or through a combination of both. The cement has a higher strength than the glass ionomer cements and it is also insoluble in the oral cavity. One draw back of this type of cement is that the process is technique sensitive.

Suppliers

J. Morita USA supplies several different types of cements, including Bistite II DC and M-Bond. Bistite II DC is self-etching, dual-cured, resin cement that can be used for many procedures. This product can be used for cementation of metal crowns, inlays, onlays, and adhesion bridges and for cast posts and cores. Ceramic crowns, inlays, onlays, bridges, and veneers and composite crowns, inlays, and onlays can also be cemented with this material. This material has a low film thickness and high bond strength to dentin. The Bistite II DC is composed of 77% silica based fillers and 23% methacrylate. M-Bond is composed of 48% acetone and 52% methacrylates, isopropanol, and phosphoric acid monomer. It was designed for restorations that demand sufficient elasticity (Maryland bridges). This product can also be used for both metal and ceramic restorations (inlays, onlays, bridges, and crowns) cast posts and cores. M-Bond has high bonding strength and a better adhesion to metal.

Process Description

Bistite II DC

For both ceramic and metal restorations the surface should be sandblasted, ultrasonically cleaned and dried. For the precious metal components used the surface should be treated with METALTITE. With ceramic components TOKUSO CERAMIC PRIMER should be applied to the surface and allowed to dry for 10 seconds. The two pastes are then mixed together for 10 seconds and then apply the cement (working time=4 minutes). The cement self cures and sets in 8 minutes 40 seconds.

M-Bond:

Ceramic and metal prosthesis should be alumina sandblasted, ultrasonically cleaned, and dried. Precious metal alloys should then be treated with METALTITE. For ceramic components the surface should be treated with TOKUSO CERAMIC PRIMER. The cement is mixed and the working time is 1 minute 40 seconds. Slight pressure should be applied while the cement is allowed to set which should take 4 minutes.

3M ESPE produces a RelyX ARC (Adhesive Resin Cement), which is a dual-cure resin cement. It is commonly used for bonding crowns, bridges, inlays, onlays and endodontic post cementation. These restorations can be porcelain, ceramic, composite, metal or porcelain-fused-to-metal The resin component contains BIS-GMA and triethylene glycol dimethacrylate (TEGDMA), along with zirconia/silica and fumed silica fillers for radiopacity, strength, and wear resistance. The cement is also composed of a dimethacrylate polymer, for easy flow while still maintaining shape, pigments, and a photoinitiator. The flexural strength of RelyX is 123 MPa (17.84 ksi), the compressive strength is 345.7 MPa (50.14 ksi), and the diametrical tensile strength is 77.6 MPa (11.25 ksi). The solubility for this cement is 0.3 $\mu g/mm^3$, the water sorption is 29 $\mu g/mm^3$, and the wear rate is 1 $\mu m/10,000$ cycles.

Process Description

Relyx Arc

The procedures all vary slightly depending on what kind of a restoration is used. Metal surfaces need to be abraded. Two coats of Single Bond adhesive should be used on the enamel and dentin surfaces. The cement should be mixed for 10 seconds and applied to the surface. Once the restoration is in place and excess cement removed, light curing takes place for 40 seconds or it can be self cured in 10 minutes.

Other Notes on Resin Cement

Taira el al investigated the bond strength of four resin cements and three primers to sandblasted titanium before and after 100,000 thermocycles. Two of the combinations were in the 50 MPa range: Panavia 21 ((Kuraray okayoma, Japan) with metal primer 2 (GC Corp Toyko) and Imperva duel (Shofu Inc. Kyoto, Japan) with metal primer 2. Both of these cements offer easier handing. Panavia is a two-part paste in an auto dispenser. It develops final cure when deprived of oxygen with a gel called oxyguard. For purposes related to this investigation an inert gas purge could possibly be used. Imperva, as a duel cure, allows manipulation until exposed to the correct wavelength of light. Chang et al conducted a literature review of studies on 4 META use in dentistry. This report indicates the results of studies of resin bonding to many metals and one ceramic and also discusses other adhesive monomers.

If a composite is deemed strong enough to bridge the gap between metal struts, the special monomers contained in some of the resin cements may be necessary to chemically bond to metal. The bond mechanism of these resins requires an oxide film on metal. For non-reactive metals like gold, and possibly tantalum, a surface treatment is needed. Methods investigated in dentistry to increase the bond strength and reduce microleakage, include electroplating or sputter coating with tin chromium, nickel, etc.

Tests

Samples of stainless steel and tantalum were laser cut with struts facing each other in butt fashion. After experimenting on scraps cut from sheet stock with various surface treatments and carious ceramic/liquid combinations, J. Heggestuen made 10 connected stainless steel coupons. This was done by air abrading the strut tips with alumina to remove any dross and to also aid in wetting. Creation Glaze (Klema, Austria)

was used due to its submicron frit and low firing temperature. Proform 10 modeling liquid (Renfort, Germany) was used to aid shaping and prevent evaporation. A small drop of mixed slurry was taken up on the tip of a single sable bristle under a microscope and positioned to bridge the gap. Slight vibration was applied to allow the surface tension to pull the mixture into a sphere. Samples were dried and placed into the furnace at 842° F., a vacuum was applied and the temperature was raised to 1272° F. at a rate of 100° F. per minute. The vacuum was released and held for one minute and then removed and allowed to cool.

CONCLUSION

Sample connections appeared smooth and pore free. Some of the samples performed well in pull tests at Scimed. J. Heggestuen believes that further investigation will lead to higher strengths with smaller dimensions at lower firing temperatures. The attempts to fire porcelain to tantalum resulted in damage to the metal with a scaly non-adherent reaction layer. Vita Titatium bonding agent was used. The intended use for this product is to control oxide formation. Firing at temperatures of 1472° F. left the tantalum brittle. Porcelain systems for bonding to titanium have demonstrated sufficient strength for dental applications. These systems include Vita's titan Keramic, Noritake super porcelain Ti-22, and Nobel Biocare Ticeram. To avoid affecting the chemistry of the metal a laser could possibly vitrify the ceramic connector. Dental lasers are equipped with microscopes and routinely can weld chrome cobalt within a few hundred microns from the acrylic. To demonstrate whether these techniques could be applied to make an electrically insulating, biocompatible, strong connection to metal a test was devised.

Ceramic to Metal

Tests were conducted to bond ceramic to metal at his dental research lab. Tantalum wire with a diameter of 0.015 inches was bonded to custom-made ceramic coupons. Fifteen samples were made using C&B Metabond made by Sun Medical. Coupons were made and ground flat on the area that was to be bonded and then glazed. Three different groups (5 samples each) were prepared with different treatments. The first group was cleaned and bonded. The next group was cleaned, the metal was primed with Metal Primer II (Meps—GC America) and the ceramics with etch free (4 Meta—Parkell Biomaterials). The final group was media blasted and no primers were used. A length of the wire (0.23-0.37 in.) was bonded to the top surface of the ceramic. MTS tests were attempted on these samples by gripping the ceramic on the bottom and pulling the wire from the top. Due to the way the two materials were bonded this type of test would indicate a shear stress more than a tensile stress. Unfortunately, tests on these samples were not successful. It was difficult to strongly grip the ceramic without breaking it; however, if the sample was not held strong enough the sample would simply slip out of the gripper during the tests. After several attempts with different grippers, it was determined that accurate results could not be found with this method. It was requested to J. Heggestuen that different samples be made. First going to bond tantalum wire face to face with each other to focus on the cement bond strength. These tests will also be done with titanium wire. If through these tests it is determined that the cement strength is high enough further tests can be done to decide if a stent can function appropriately with a simple cement bond holding the struts together. Further tests can also be done to determine the strength with ceramic bonded to metal through cementation.

Metal to Metal

Using the sample cements that were sent from J. Morita (M-Bond) and Bisco (C&B) tests were conducted. Tantalum wire (0.020-inch diameter) was used for these tests. Half-inch sections were cut and ground with 800-grit paper. Different methods were tried in order to find a way to bond the wire face-to-face. It was finally decided that aluminum blocks with a slit cut to the 0.02-inch diameter would work the best to cement the samples together. Tensile tests were done on 5 of the M-Bond specimens, but results were hard to calculate because the cement was not uniform on the samples and accounted for more surface area than the wire face. With a rough estimation that the cement was twice the diameter of the wire, it was determined that the tensile strength was between 3000-3800 psi. If this number is accurate, it is not high enough for the required stress of 10 ksi. However, several factors could influence these results including; incorrect surface area, surface not sandblasted (as recommended by the suppliers), and no primer was used. At this point one can not accept nor eliminate cementation as a possible method. The detailed descriptions of the tests that were attempted to cement the wire together are given in the Appendix.

Ground Metal

Currently, Ti-6Al-4V wire (diameter 0.010 inch) is being ground down at the ends to a diameter of 0.006 inches. There will be a step down from the higher diameter to the lower one. The smaller ground portion will have a length of about 1-inch, which can be cut to a specific length at a later point. These wire pieces can be used to test the design idea of having a narrowed portion in the stent where ceramic can be fired on and then laser portion a section out [FIG. 4]. Once these wire pieces are obtained, a way to fire on the ceramic must be determined and tested.

What is claimed is:

1. A medical device for use within a body cavity, the medical device having a visualization region in which visualization using magnetic resonance imaging (MRI) is desired, the medical device comprising:
    structural material defining a primary structure having a wall with openings therein and a periphery, the structural material being configured such that any closed path, in the visualization region, extending about at least one of the periphery or an opening in the wall, passes through at least two materials, wherein at least one of the materials comprises a substantially low magnetic susceptibility material.

2. The medical device of claim 1 wherein the primary structure comprises a generally tubular structure which comprises:
    a plurality of electrically conductive structural members; and
    a plurality of bridges coupled to and forming electrical discontinuities in the plurality of electrically conductive structural members, the electrical discontinuities being sufficient to enable MRI visualization in the visualization region.

3. The medical device of claim 2 wherein the plurality of electrically conductive structural members are arranged as a plurality of electrically conductive cells that define the openings in the wall.

4. The medical device of claim 3 wherein each of the plurality of conductive cells is coupled to at least one of the plurality of bridges such that any closed path defining the cell in the visualization region passes through the at least one bridge, inhibiting formation of an electrical loop in the visualization region.

5. The medical device of claim 4 wherein the plurality of electrically conductive structural members further include a plurality of electrically conductive connectors, with each of the plurality of connectors connecting at least two of the plurality of cells.

6. The medical device of claim 5 wherein each of the plurality of connectors is coupled to at least one of the plurality of bridges, thereby preventing an electrical loop being formed between two or more cells across at least one of the plurality of connectors.

7. The medical device of claim 2 wherein the plurality of bridges comprise a ceramic material.

8. The medical device of claim 2 wherein the plurality of bridges comprise a polymeric material.

9. The medical device of claim 2 wherein the plurality of bridges comprise an electrically non-conductive cement.

10. The medical device of claim 2 wherein the plurality of bridges comprise an electrically non-conductive adhesive.

11. The medical device of claim 2 wherein the substantially low magnetic susceptibility material is at least one of platinum, iridium, tantalum, titanium, niobium, hafnium and gold.

12. The medical device of claim 2 and further comprising a coating of electrically insulating material covering at least portions of the plurality of electrically conductive structural members which are immediately adjacent to the bridges.

13. The medical device of claim 12 wherein the insulating material is a polymeric material.

14. The medical device of claim 12 wherein the insulating material is a ceramic material.

15. The medical device of claim 2 wherein the plurality of bridges are formed in portions of the medical device which exhibit lower tensile stress, when the medical device is extended, relative to other portions of the medical device.

16. The medical device of claim 2 wherein the plurality of electrically conductive structural members comprise a metal/ceramic/metal layered structure.

17. The medical device of claim 16 wherein the plurality of bridges comprise one or more slits formed in metal layers of the metal/ceramic/metal layered structure.

18. The medical device of claim 17 wherein the slits are not formed in the ceramic layer of the metal/ceramic/metal layered structure.

19. The medical device of claim 17 and further comprising an electrically isolating layer formed on the metal layers and in the slits.

20. The medical device of claim 17 wherein for each of the plurality of electrically conductive structural members, a slit formed in a first metal layer of the layered structure is spaced apart from a slit formed in a second metal layer of the layered structure, such that at every position along a length of the electrically conductive structural member, the structural member includes the ceramic layer and at least one of the metal layers.

21. The medical device of claim 2 and further comprising a plurality of sleeves, with each of the plurality of sleeves positioned over one of the plurality of bridges and overlapping with adjacent portions of a corresponding electrically conductive structural member.

\* \* \* \* \*